(12) United States Patent
Staudt et al.

(10) Patent No.: US 8,748,114 B2
(45) Date of Patent: Jun. 10, 2014

(54) ZAP-70 EXPRESSION AS A MARKER FOR CHRONIC LYMPHOCYTIC LEUKEMIA / SMALL LYMPHOCYTIC LYMPHOMA (CLL/SLL)

(75) Inventors: Louis M. Staudt, Silver Spring, MD (US); Andreas Rosenwald, Bethesda, MD (US); Wyndham Wilson, Washington, DC (US); Todd S. Barry, Seattle, WA (US); Adrian Wiestner, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 135 days.

(21) Appl. No.: 13/155,198

(22) Filed: Jun. 7, 2011

(65) Prior Publication Data

US 2011/0236915 A1   Sep. 29, 2011

Related U.S. Application Data

(62) Division of application No. 11/955,322, filed on Dec. 12, 2007, now Pat. No. 7,981,610, which is a division of application No. 10/309,548, filed on Dec. 3, 2002, now Pat. No. 7,329,502.

(60) Provisional application No. 60/375,966, filed on Apr. 25, 2002.

(51) Int. Cl.
  *G01N 33/574* (2006.01)

(52) U.S. Cl.
  USPC ............ 435/7.23; 435/7.1; 435/7.2; 530/350; 530/387.1; 530/389.1

(58) Field of Classification Search
  USPC .............. 530/350, 387.1, 389.1; 435/7.1, 7.2, 435/7.23
  See application file for complete search history.

(56) References Cited

U.S. PATENT DOCUMENTS

| | | | |
|---|---|---|---|
| 5,776,696 | A | 7/1998 | Salowe |
| 5,783,398 | A | 7/1998 | Marcy et al. |
| 6,251,620 | B1 | 6/2001 | Hatada et al. |

FOREIGN PATENT DOCUMENTS

| | | |
|---|---|---|
| WO | WO 98/45704 | 10/1998 |
| WO | WO 00/27428 | 5/2000 |
| WO | WO 01/55307 | 8/2001 |
| WO | WO 01/64886 | 9/2001 |
| WO | WO 01/94629 | 12/2001 |
| WO | WO 02/14281 | 2/2002 |

OTHER PUBLICATIONS

De Plaen et al. (Immunogenetics. 1994; 40: 360-369).*
Bowie et al. (Science. Mar. 16, 1990; 247 (4948): 1306-1310).*
Ando et al. (Leuk. Lymphoma. Jan. 2004; 45 (1): 193-8).*
Ellis et al. (Blood. Jun. 1979; 53 (6): 1066).*
Chan et al. (J. Immunol. May 15, 1994; 152 (10): 4758-66).*
Vroblova et al. (Hematology. Sep. 2012; 17 (5): 268-74).*
Wang et al. (Clin. Exp. Med. Jun. 2012; 12 (2): 69-77).*
Nolz et al. (Leukemia. Jun. 2005; 19 (6): 1018-24).*
Cutrona et al. (Eur. J. Immunol. Mar. 2006; 36 (3): 558-69).*
Scielzo et al. (Leukemia. Apr. 2006; 20 (4): 689-95).*
Kay et al. (Cytometry B Clin. Cytom. Jul. 15, 2006; 70 (4): 218-26).*
Marquez et al. (Int. J. Lab. Hematol. Apr. 2011; 33 (2): 194-200).*
Letestu et al. (Cytometry B Clin. Cytom. Jul. 15, 2006; 70 (4): 309-14).*
Hoyer et al. (Blood. Aug. 1, 1995; 86 (3): 1163-9).*
Sup et al. (Am. J. Clin. Pathol. Oct. 2004; 122 (4): 582-7).*
Badea et al. (Rom. J. Morphol. Embryol. 2010; 51 (2): 353-8).*
Skolnick et al. (Trends in Biotechnology 2000; 18: 34-39).*
Burgess et al. (Journal of Cell Biology 1990; 111: 2129-2138).*
Lazar et al. (Molecular and Cellular Biology, 1988, 8: 1247-1252).*
Luque et al. (Biochemistry. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Bannerji et al., "Update on the Biology of Chronic Lymphocytic Leukemia," *Curr. Opin. Oncol.* 12:22-29, 2000.
Branch, "A good antisense molecule is hard to find", *Trends Biochem. Sci.*, vol. 23, pp. 45-50, 1998.
Caligaris-Cappio et al., "B-cell Chronic Lymphocytic Leukemia: A Bird of a Different Feather," *J. Clin. Oncol.* 17(1):399-408, Jan. 1999.
Caligaris-Cappio, "Biology of Chronic Lymphocytic Leukemia," *Rev. Clin. Exp. Hematol.* 4(1):5-21, 2000.
Capello et al., "Identification of Three Subgroups of B Cell Chronic Lymphocytic Leukemia Based Upon Mutations of BCL-6 and IgV Genes," *Leukemia* 14(5):811-815, May 2000.
Catherwood et al., "ZAP-70 mRNA quantification in B-cell chronic lymphocytic leukaemia," *Eur. J Haematol.*, vol. 76, pp. 294-298, 2006.
Chan et al., "ZAP-70: a 70 kd Protein-Tyrosine Kinase That Associates with the TCR Zeta Chain," *Cell* 71(4):649-662, Nov. 1992.
Chen et al., "Expression of ZAP-70 is associated with increased B-cell receptor signaling in chronic lymphocytic leukemia," *Blood*, vol. 100, No. 13, pp. 4609-4614, 2002.
Crespo et al., "ZAP-70 Expression as a Surrogate for Immunoglobulin-Variable-Region Mutations in Chronic Lymphocytic Leukemia," *New England Journal of Medicine*, vol. 348, pp. 1764-1775, 2003.

(Continued)

*Primary Examiner* — Stephen Rawlings
(74) *Attorney, Agent, or Firm* — Klarquist Sparkman, LLP

(57) ABSTRACT

It has been surprisingly found that ZAP-70 expression, both at the protein and mRNA levels, is indicative of clinical subgroups of CLL/SLL patients. In particular, high ZAP-70 expression is indicative of Ig-unmutated CLL/SLL. Methods are provided for discriminating between clinical subgroups of CLL/SLL, by determining whether subjects overexpress ZAP-70 mRNA or protein.

20 Claims, 5 Drawing Sheets

(56) References Cited

OTHER PUBLICATIONS

D'Arena et al., "CD69 Expression in B-Cell Chronic Lymphocytic Leukemia: A New Prognostic Marker?" *Haematolgica* 86:995-996, Sep. 2001.
Damle et al., "Ig V Gene Mutation Status and CD38 Expression as Novel Prognostic Indicators in Chronic Lymphocytic Leukemia," *Blood* 94:1840-1847, 1999.
Damle et al., "Updated Data on V Gene Mutation Status and CD38 Expression in B-CLL," *Blood* 95:2456-2457, 2000 (Response to Hamblin, 2000).
De Plaen et al., "Structure, chromosomal localization, and expression of 12 genes of the Mage family," *Immunogenetics* vol. 40, pp. 360-369, 1994.
Fargnoli et al., "Diminished TCR Signaling in Cutaneous T Cell Lymphoma is Associated With Decreased Activities of Zap70, Syk and Membrane-Associated Csk," *Leukemia* 11(8)1338-1346, Aug. 1997.
Garcia et al., "Diagnostic Usefulness of CD23 and FMC-7 Antigen Expression Patterns in B-cell Lymphoma Classification," *Am. J. Clin. Pathol.* 115:258-265, Feb. 2001.
Gauen et al., "Interactions of p59$^{fyn}$ and ZAP-70 with T-Cell Receptor Activation Motifs: Defining the Nature of a Signaling Motif", *Molecular and Cellular Biology*, vol. 14, No. 6, pp. 3729-3741, 1994.
GenBank Accession No. L05148, Aug. 3, 1993.
GenBank Accession No. XM_047776, Feb. 7, 2002.
Hamblin et al., "Immunoglobulin V Genes and CD38 Expression in CLL," *Blood* 95:2455-2456, 2000.
Hamblin et al., "Unmutated Ig V$_H$ Genes Are Associated With a More Aggressive Form of Chronic Lymphocytic Leukemia," *Blood* 94(6):1848-1854, Sep. 15, 1999.
Kim et al., "Expression of ZAP-70 Protein Correlates with Disease Stage in Chronic Lymphocytic Leukemia and is Associated with, but not Generally Restricted to, Non-mutated Ig V$_H$ Status," *Leuk. Lymphoma* vol. 45, pp. 2037-2045, 2004.
Klein et al., "Gene Expression Profiling of B Cell Chronic Lymphocytic Leukemia Reveals a Homogeneous Phenotype Related to Memory B Cells," *J. Exp. Med.*, vol. 194, No. 11, pp. 1625-1638, 2001.
Knauf et al., "Prognostic Impact of the Serum Levels of Soluble CD23 in B-Cell Chronic Lymphocytic Leukemia," *Blood* 89(11):4241-4242, 1997.
Koyasu et al., "Delineation of a T-cell Activation Motif Required for Binding of Protein Tyrosine Kinases Containing Tandem SH2 Domains," *Proc. Natl. Acad. Sci. USA* 91:6693-6697, Jul. 1994.
Kuroyama et al., "Identification of a novel isoform of ZAP-70, truncated ZAP kinase," *Biochem. Biophys. Res. Comm.* vol. 315, pp. 835-941, 2004.
Kurt et al., "Peripheral T lymphocytes from women with breast cancer exhibit abnormal protein expression of several signaling molecules," *Int. J. Cancer* vol. 78, pp. 16-20, 1998.
Longo et al., "The Akt signaling pathway determines the different proliferative capacity of chronic lymphocytic leukemia B-cells from patients with progressive and stable disease", *Leukemia*, vol. 21, pp. 110-120, 2007.
Naylor and Capra, "Mutational Status of Ig V$_H$ Genes Provides Clinically Valuable Information in B-Cell Chronic Lymphocytic Leukemia," *Blood* 94(6):1837-1839, Sep. 15, 1999.
Nel et al., "Ligation of the T-cell Antigen Receptor (TCR) Induces Association of hSos1, ZAP-70, Phospolipase C-γ1, and Other Phosphoproteins with Grb2 and the ζ-Chain of the TCR," *J. Biol. Chem.* 270(31):18428-18436, Aug. 4, 1995.
Northrop et al., "Characterization of the Roles of SH2 Domain-Containing Proteins in T-Lymphocyte Activation by Using Dominant Negative SH2 Domains," *Mol. Cell. Biol.* 16(5):2255-2263, 1996.
Orchard et al., "ZAP-70 in B Cell Malignancies," *Leuk. Lymphoma* vol. 46, pp. 1689-1698, 2005.
Orchard et al., "ZAP-70 expression and prognosis in chronic lymphocytic leukaemia," *The Lancet* vol. 363, pp. 105-111, 2004.
Pasqualucci et al., "BCL-6 Mutations are Associated With Immunoglobulin Variable Heavy Chain Mutations in B-cell Chronic Lymphocytic Leukemia." *Cancer Res.* 60(20):5644-5648, Oct. 15, 2000.
Paz et al., "Mapping the Zap-70 Phosphorylation Sites on LAT (linker for activation of T cells) Required for Recruitment and Activation of Signaling Proteins in T Cells," *Biochem. J.* 356:461-471, 2001.
Rassenti and Kipps, "Expression of Ig-β (CD79b) by Chronic Lymphocytic Leukemia B Cells That Lack Immunoglobulin Heavy-Chain Allelic Exclusion," *Blood* 95(8):2725-2727, Apr. 15, 2000.
Rassenti and Kipps, "Lack of Extensive Mutations in the VH5 Genes Used in Common B Cell Chronic Lymphocytic Leukemia," *J Exp. Med.* 177(4):1039-1046, Apr. 1, 1993.
Rassenti et al., "ZAP-70 Compared with Immunoglobulin Heavy-Chain Gene Mutation Status as a Predictor of Disease Progression in Chronic Lymphocytic Leukemia," *N. Engl. J Med.* vol. 351, pp. 893-901, 2004.
Rosenwald et al., "Relation of Gene Expression Phenotype to Immunoglobulin Mutation Genotype in B Cell Chronic Lymphocytic Leukemia," *J. Exp. Med.*, vol. 194, No. 11, pp. 1639-1647, 2001.
Sarfati et al., "Prognostic Importance of Serum Soluble CD23 Level in Chronic Lymphocytic Leukemia," *Blood* 88(11):4259-4264, Dec. 1, 1996.
Skolnick et al., "From genes to protein structure and function: novel applications of computational approaches in the genomic era," *Trends in Biotechnology* vol. 18, pp. 34-39, 2000.
Swerdlow, "Small B-Cell Lymphomas of the Lymph Nodes and Spleen: Practical Insights to Diagnosis and Pathogenesis," *Mod. Pathol.* 12(2):125-140, 1999.
Toyabe et al., "Specific immunoglobulin E responses in ZAP-70-deficient patients are mediated by Syk-dependent T-cell receptor signalling", *Immunology*, vol. 103, pp. 164-171, 2001.
Tworek et al., "Flow Cytometric and Immunohistochemical Analysis of Small Lymphocytic Lymphoma, Mantle Cell Lymphoma, and Plasmacytoid Small Lymphocytic Lymphoma," *Am. J. Clin. Pathol.* 110(5):582-589, 1998. Abstract Only.
Ulivieri et al., "Restoration of thymic development in an Lck(−/−) thymoma overexpressing ZAP-70", *Mol. Immunol.*, vol. 37, No. 1-2, pp. 85-90, 2000, Abstract Only.
Voss et al., "Correlation of Clinical Data with Proteomics Profiles in 24 Patients with B-Cell Chronic Lymphocytic Leukemia," *Int. J. Cancer* 91:180-186, 2001.
Wang, "Wang web page," http://www.bloodctrwise.org/research/faculty/Wang/wang.html, pp. 1-4, accessed Mar. 4, 2002.
Weil et al., "Altered Expression of Tyrosine Kinases of the Src and Syk Families in Human T-Cell Leukemia Virus Type 1-Infected T-Cell Lines", *Journal of Virology*, vol. 73, No. 5, p. 9. 3709-3717, 1999.
Weistner et al., "ZAP-70 expression identifies a chronic lymphocytic leukemia subtype with unmutated immunoglobulin genes, inferior clinical outcome, and distinct gene expression profile," *Blood*, vol. 101, No. 12, pp. 4944-4951, 2003.
Wiestner, "More ZAP for chronic lymphocytic leukemia (CLL)," *Blood* vol. 105, pp. 1839-1840, 2005.
Wiestner et al., "Zap70 Expression is a Distinctive Feature of B-CLL With Unmutated Immunoglobulin Genes and Can Be Useful for Diagnostic Application," 70éme Assemblee annuelle de la SSMI / 70. Jahresversammlung der SGIM (Société Suisse de la Médecine Interne (SSMI)), Abstract, available on Internet as early as Apr. 25, 2002.
Xu et al., "Assessment of CD10 in the Diagnosis of Small B-Cell Lymphomas: A Multiparameter Flow Cytometric Study," *Am. J Clin. Pathol.* 117(2):291-300, Feb. 2002.
Zhang and Siraganian, "CD45 is Essential for FcεRI Signaling by ZAP70, but not Syk, in Syk-Negative Mast Cells," *J. Immunol.* 163:2508-2516, 1999.

\* cited by examiner

ZAP-70 EXPRESSION AS A MARKER FOR CHRONIC LYMPHOCYTIC LEUKEMIA / SMALL LYMPHOCYTIC LYMPHOMA (CLL/SLL)

CROSS REFERENCE TO RELATED APPLICATIONS

This is a divisional of U.S. patent application Ser. No. 11/955,322, filed on Dec. 12, 2007, issued as U.S. Pat. No. 7,981,610 on Jul. 19, 2011, which is a divisional of U.S. patent application Ser. No. 10/309,548, filed on Dec. 3, 2002, issued as U.S. Pat. No. 7,329,502 on Feb. 12, 2008, which claims the benefit of U.S. Provisional Application No. 60/375,966, filed on Apr. 25, 2002, all of which are herein incorporated by reference in their entirety.

FIELD

This disclosure relates to methods of diagnosis and detection of cancers, and more particularly to distinguishing types of CLL/SLL based on the level of ZAP-70 protein or nucleic acid in a biological sample

BACKGROUND

Chronic lymphocytic leukemia/small lymphocytic lymphoma (CLL/SLL) is a malignancy of B-lymphocytes in the blood, bone marrow, and lymph nodes with a characteristic immunophenotype. The recent WHO classification discusses CLL/SLL as an entity but notes that the term SLL is restricted to cases with the tissue morphology and immunophenotype of CLL, but which are non-leukemic (*WHO Classification of Tumours. Tumours of Haemotopoietic and Lymphoid Tissue*. Edited by Jaffe, Harris, Stein, Vardiman. IARC Press 2001). The clinical course of CLL is quite varied. While some patients have a chronic lymphocytosis without any need for therapeutic interventions, other patients may die rapidly despite aggressive treatment. The classic staging systems provide only limited prognostic information in newly diagnosed patients.

Recently, the presence or absence of somatic mutations in the immunoglobulin (Ig) variable region genes has been shown to distinguish between two disease subsets conferring important prognostic information. A median survival of 95 months was found in patients with unmutated Ig genes versus 293 months in patients with mutated Ig genes (Hamblin, *Blood* 94(6):1848-1854, 1999). Unfortunately, the ability to sequence Ig genes is not available in most clinical laboratories.

In addition to mutated Ig genes, several other potential diagnostic or prognostic markers have been identified for CLL, as well as for other small B-cell lymphomas. By way of example, these include CD10, CD20, CD21, CD23 (including serum CD23), CD38, CD69, CD43, FMC-7, and BCL-6. The research and medical communities are actively searching for good prognostic markers, but as yet no definitive markers have been identified.

SUMMARY

This disclosure provides a method of detecting a biological condition associated with ZAP-70 overexpression in a subject. Also provided herein are methods to determine whether a subject has ZAP-70 nucleic acid or ZAP-70 protein overexpression. It is shown herein that the biological condition associated with ZAP-70 overexpression is Ig-unmutated CLL.

The disclosure also provides a method of modifying a level of expression of a ZAP-70 protein in a subject in order to reduce, ameliorate, or control CLL. Examples of these methods include expressing in the subject a recombinant genetic construct including a promoter operably linked to a nucleic acid molecule where expression of the nucleic acid molecule changes expression of the ZAP-70 protein. In one embodiment, the nucleic acid molecule includes at least 15 consecutive nucleotides of the nucleotide sequence shown in SEQ ID NO: 1. In another embodiment, the nucleic acid sequence includes a sequence at least 85% identical to SEQ ID NO: 1.

Also provided herein are kits for determining whether or not a subject has a biological condition associated with ZAP-70 overexpression. In one embodiment, the kit is an in vitro assay kit. These kits can be used to detect an overabundance of ZAP-70 protein or nucleic acid in a sample of tissue and/or body fluids from the subject. For example, the kits can include a container with an antibody specific for ZAP-70 protein and instructions for using the kit. The instructions can indicate the steps for performing a method to detect the presence of ZAP-70 protein or nucleic acid in the sample as well as how to analyze data generated by the method. In one embodiment, the instructions indicate that overabundance of ZAP-70 protein in the sample indicates that the individual has or is predisposed to a biological condition.

The foregoing and other features and advantages will become more apparent from the following detailed description of several embodiments, which proceeds with reference to the accompanying figures.

BRIEF DESCRIPTION OF THE FIGURES

FIG. 1A shows the performance of the predictor using a cross-validation strategy.

In FIG. 5A, ZAP-70 protein expression was assessed by Western blotting in whole cell lysates of normal peripheral blood mononuclear cells (PBMC), or CD19+ purified leukemic cells from blood of patients with Ig-unmutated and Ig-mutated CLL. The data are representative of Western blot analysis of 20 patient samples analyzed. Equal loading is demonstrated by probing for beta-tubulin.

SEQUENCE LISTING

Informal

Figure 1A:
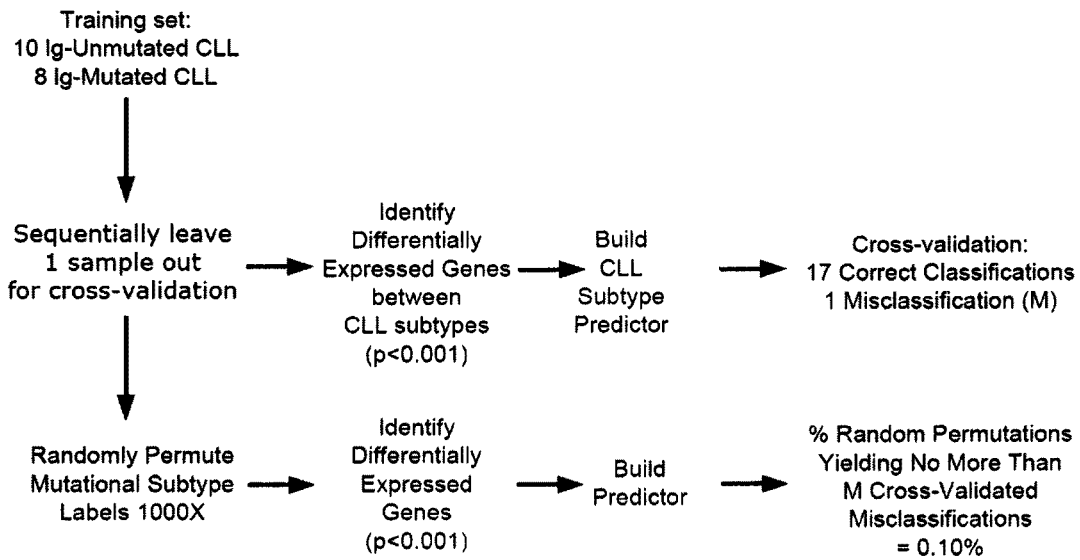
FIGS. 1A and B is a series of schematic drawings showing the statistical methodology for the creation and validation of an Ig-mutational status predictor in CLL.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows a cDNA encoding ZAP-70.

SEQ ID NO: 2 shows the amino acid sequence of ZAP-70.

SEQ ID NO: 3 shows the forward or upstream ZAP-70 oligonucleotide primer (5' TCTCCAAAGCACTGGGTG 3').

SEQ ID NO: 4 shows the reverse or downstream ZAP-70 oligonucleotide primer (5' AGCTGTGTGTGGAGACAAC-CAAG 3').

SEQ ID NO: 5 shows the forward or upstream VH1 and VH7 primer (5'-CCA TGG ACT GGA CCT GGA-3').

SEQ ID NO: 6 shows the forward or upstream VH2 primer (5'-ATG GAC ATA CTT TGT TCC AC-3').

SEQ ID NO: 7 shows the forward or upstream VH3 primer (5'-CCA TGG AGT TTG GGC TGA GC-3').

SEQ ID NO: 8 shows the forward or upstream VH4 primer (5'-ATG AAA CAC CTG TGG TTC TT-3').

SEQ ID NO: 9 shows the forward or upstream VH5 primer (5'-ATG GGG TCA ACC GCC ATC CT-3').

SEQ ID NO: 10 shows the forward or upstream VH6 primer (5'-ATG TCT GTC TCC TTC CTC AT-3').

SEQ ID NO: 11 shows a 3' oligonucleotide complementary to the JH consensus sequence (5'-ACC TGA GGA GAC GGT GAC C-3') as a reverse or downstream primer.

SEQ ID NO: 12 shows the constant region of the IgM locus (5'-AGG AGA AAG TGA TGG AGT CG-3') as a reverse or downstream primer.

SEQ ID NO: 13 shows the forward ZAP-70 primer.

SEQ ID NO: 14 shows the reverse ZAP-70 primer.

SEQ ID NO: 15 shows the ZAP-70 FAM™-probe.

SEQ ID NO: 16 shows the framework region (FR)1-VH1 forward primer.

SEQ ID NO: 17 shows the framework region (FR)1-VH2 forward primer.

SEQ ID NO: 18 shows the framework region (FR)1-VH3 forward primer.

SEQ ID NO: 19 shows the framework region (FR)1-VH4 forward primer.

SEQ ID NO: 20 shows the framework region (FR)1-VH5 forward primer.

SEQ ID NO: 21 shows the framework region (FR)1-VH6 forward primer.

DETAILED DESCRIPTION

I. Abbreviations

| BCR | B cell receptor |
|---|---|
| B-CLL | B cell CLL |
| CLL | chronic lymphocytic leukemia |
| DLBCL | diffuse large B cell lymphoma |
| FGFR | fibroblast growth factor receptor |
| H | heavy |
| IgV | Ig variable region |
| M-CLL | IgV-mutated CLL |
| PBMC | peripheral blood mononuclear cells |
| PKC | protein kinase C |
| RT-PCR | reverse transcription polymerase chain reaction |
| SLL | small lymphocytic lymphoma |
| TCR | T cell antigen receptor |
| UM-CLL | IgV-unmutated CLL |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Antisense, Sense, and Antigene: Double-stranded DNA (dsDNA) has two strands, a 5'→3' strand, referred to as the plus strand, and a 3'→5' strand (the reverse complement), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In vitro amplification: Techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein, cell, or organelle) has been substantially separated or purified away from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by phosphodiester bonds, between about 6 and about 500 nucleotides in length. An oligonucleotide analog refers to moieties that function similarly to oligonucleotides but have non-naturally occurring portions. For example, oligonucleotide analogs can contain altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Peptide Nucleic Acid (PNA): An oligonucleotide analog with a backbone comprised of monomers coupled by amide (peptide) bonds, such as amino acid monomers joined by peptide bonds.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the ZAP-70 sequences described herein, for example, by using computer programs intended for that purpose such as Primer (Version 0.5, 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a ZAP-70 protein-encoding nucleotide will anneal to a target sequence, such as another homolog of the designated ZAP-70 protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a ZAP-70 protein-encoding nucleotide sequences.

Also provided are isolated nucleic acid molecules that comprise specified lengths of the disclosed ZAP-70 nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a ZAP-70 nucleic acid may be apportioned into halves or quarters based on sequence length, and isolated nucleic acid molecules may be derived from the first or second halves of the molecules, or any of the four quarters, etc.). A ZAP-70 cDNA or other encoding sequence also can be divided into smaller regions, e.g. about eighths, sixteenths, twentieths, fiftieths, and so forth, with similar effect.

Another mode of division is to select the 5' (upstream) and/or 3' (downstream) region associated with a ZAP-70 gene.

Protein: A biological molecule expressed by a gene or recombinant or synthetic coding sequence and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production/reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A recombinant organism or cell is one that comprises at least one recombinant nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of human ZAP-70 protein, and the corresponding cDNA or gene sequence, will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a human ZAP-70 protein-encoding sequence will typically hybridize to a probe based on either an entire human ZAP-70 protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of 0- to about 5-nucleotides, wherein the sequence of the double stranded RNAs is essentially identical to a portion of a coding region of the target gene for which interference or inhibition of expression is desired. The double stranded RNAs can be formed from complementary ssRNAs or from a single stranded RNA that forms a hairpin or from expression from a DNA vector.

Specific binding agent: An agent that binds substantially only to a defined target. Thus a protein-specific binding agent binds substantially only the specified protein. By way of example, as used herein, the term "ZAP-70-protein specific binding agent" includes anti-ZAP-70 protein antibodies (and functional fragments thereof) and other agents (such as soluble receptors) that bind substantially only to the ZAP-70 protein.

Anti-ZAP-70 protein antibodies may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-ZAP-70 protein monoclonal antibody, binds substantially only to the ZAP-70 protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means include A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

III Overview of Several Embodiments

The inventors have discovered that ZAP-70 is expressed at high levels in the B-cells of CLL/SLL patients, and more particularly in the subset of CLL which tends to have a more aggressive clinical course that is especially in CLL/SLL patients with unmutated Ig genes. Because of the correlation between ZAP-70 expression levels and Ig gene mutation status, ZAP-70 can be used as a prognostic indicator to identify those patients likely to have severe disease (high ZAP-70, unmutated Ig genes), and who are therefore candidates for aggressive therapy.

Detecting ZAP-70 protein expression, for instance by Western blotting, immunohistochemistry, flow cytometry, or immunofluorescence, can serve as easily performed assays to distinguish the two groups of CLL patients. Further, ZAP-70 is useful as a target for therapeutic strategies, either directly or as an indicator of a type of CLL that responds to certain treatments.

In another embodiment, ZAP-70 RNA levels can be used similarly to ZAP-70 protein levels.

One embodiment is a method of detecting a biological condition associated with ZAP-70 overexpression in a subject, which method involves determining whether the subject has ZAP-70 nucleic acid or ZAP-70 protein overexpression, wherein the biological condition comprises Ig-unmutated CLL. Examples of this method are methods of predicting a predisposition to poor clinical outcome in a subject. Such methods involve determining whether the subject overexpresses ZAP-70 protein, wherein presence of ZAP-70 protein overexpression indicates the predisposition to poor clinical outcome.

Specific examples of the methods of detecting a biological condition associated with ZAP-70 involve reacting at least one ZAP-70 molecule contained in a sample (e.g., one containing a neoplastic cell) from the subject with a reagent comprising a ZAP-70-specific binding agent to form a ZAP-70:agent complex. In examples of these methods, the ZAP-70 molecule is a ZAP-70 encoding nucleic acid or a ZAP-70 protein. The ZAP-70 specific binding agent is, in some embodiments, a ZAP-70 oligonucleotide or a ZAP-70 protein specific binding agent.

In another embodiment, the method further involves in vitro amplifying a ZAP-70 nucleic acid prior to detecting the abnormal ZAP-70 nucleic acid. By way of example, the ZAP-70 nucleic acid is in vitro amplified using at least one oligonucleotide primer derived from a ZAP-70-protein encoding sequence. Examples of such oligonucleotide primers comprise at least 15 contiguous nucleotides from SEQ ID NO: 1.

Another embodiment is a method of detecting a biological condition associated with ZAP-70 overexpression in a subject, wherein the ZAP-70 molecule is a ZAP-70 encoding sequence. In such methods, the binding agent is optionally a labeled nucleotide probe. For instance, examples of such nucleotide probes have a sequence selected from the group consisting of: SEQ ID NO: 1; nucleic acid sequences having at least 85% sequence identity with SEQ ID NO: 1; and fragments thereof at least 15 nucleotides in length.

Another embodiment is a method of detecting a biological condition associated with ZAP-70 overexpression in a subject, wherein the ZAP-70 molecule is a ZAP-70 protein. In representative examples of such methods, the complexes are detected by Western blot assay, or by ELISA. By way of example, the ZAP-70 protein in such methods may include a sequence selected from the group consisting of: SEQ ID NO: 2; amino acid sequences having at least 85% sequence identity with SEQ ID NO: 2; and conservative variants thereof.

In a further embodiment is a method of treating a subject overexpressing ZAP-70, wherein the method involves administering to the subject a therapeutically effective amount of an agent that inhibits ZAP-70 function or expression. In specific examples, the agent inhibits ZAP-70 expression or ZAP-70 function. In other specific examples, the agent is an oligonucleotide that is homologous to a nucleic acid sequence as set forth as SEQ ID NO: 1. The agent can also be a kinase inhibitor or a drug that affects the ability of ZAP-70 to interact with other proteins. Such methods involve treating subjects for Ig-unmutated chronic lymphocytic leukemia associated with ZAP-70 overexpression.

In still further examples, the ZAP-70-specific binding agent is a ZAP-70-specific antibody (e.g., a monoclonal antibody) or a functional fragment thereof.

Also provided herein are kits for detecting overexpression of ZAP-70 protein in a subject (such as a mammal, for instance a human). Examples of such kits comprising a ZAP-70 protein specific binding agent, for instance a specific binding agent is capable of specifically binding to an epitope within the amino acid sequence shown in SEQ ID NO: 2; amino acid sequences that differ from those specified in SEQ ID NO: 2 by one or more conservative amino acid substitutions; amino acid sequences having at least 85% sequence identity to; or antigenic fragments of in of these.

Still further example kits include a means for detecting binding of the ZAP-70 protein binding agent to a ZAP-70 polypeptide.

Specific examples of provided kits include as part of the kit an amount of a ZAP-70 protein binding agent, and the agent is an antibody.

Another embodiment is a kit for determining whether or not a subject has a biological condition associated with ZAP-70 overexpression, by detecting an overabundance of ZAP-70 protein or nucleic acid in a sample of tissue and/or body fluids from the subject. Examples of this kit include as elements of the kit a container comprising an antibody specific for ZAP-70 protein or an oligonucleotide homologous to a ZAP-70 nucleic acid; and instructions for using the kit, the instructions indicating steps for: performing a method to detect the presence of ZAP-70 protein or nucleic acid in the sample; and analyzing data generated by the method, wherein the instructions indicate that overabundance of ZAP-70 protein or nucleic acid in the sample indicates that the individual has or is predisposed to the biological condition. Optionally, such kits may further include a container that comprises a detectable antibody capable of binding to the ZAP-70 protein specific antibody or a container that comprises a labeled nucleotide probe capable of specifically hybridizing to the ZAP-70 nucleic acid.

A still further embodiment is an in vitro assay kit for determining whether or not a subject has a biological condition associated with an abnormal ZAP-70 expression. Such kits include a container comprising a ZAP-70 protein specific antibody or an oligonucleotide homologous to a ZAP-70 nucleic acid; a container comprising a negative control sample; and instructions for using the kit, the instructions indicating steps for: performing a test assay to detect a quantity of ZAP-70 protein or nucleic acid in a test sample of tissue and/or bodily fluid from the subject, performing a negative control assay to detect a quantity of ZAP-70 protein or nucleic acid in the negative control sample; and comparing data generated by the test assay and negative control assay, wherein the instructions indicate that a quantity of ZAP-70 protein or nucleic acid in the test sample more than the quantity of ZAP-70 protein or nucleic acid in the negative control sample indicates that the subject has the biological condition. Optionally, such kits may further include a container that comprises a detectable antibody capable of binding to the ZAP-70 protein specific antibody or a container that comprises a labeled nucleotide probe capable of specifically hybridizing to the ZAP-70 nucleic acid.

In specific examples of the provided kits, the biological condition associated with abnormal ZAP-70 expression (e.g., overexpression) is Ig unmutated-CLL.

Also provided are methods of modifying a level of expression of a ZAP-70 protein in a subject in order to reduce, ameliorate, or control CLL, which method involves expressing in the subject a recombinant genetic construct comprising a promoter operably linked to a nucleic acid molecule, wherein the nucleic acid molecule comprises at least 15 consecutive nucleotides of the nucleotide sequence shown in SEQ ID NO: 1, or a sequence at least 85% identical to SEQ ID NO: 1, and expression of the nucleic acid molecule changes expression of the ZAP-70 protein. In examples of such methods, the nucleic acid molecule is in antisense orientation relative to the promoter.

IV. ZAP-70

ZAP-70 (GenBank Accession no. XM_047776) is a member of the ZAP-70/Syk family of protein tyrosine kinases. ZAP-70 is expressed in T-cells and natural killer cells, while Syk is present in most hematopoietic cells, including B cells, mast cells, immature T cells, and platelets. ZAP-70 and Syk are structurally similar, and their cellular functions may partially overlap (Zhang and Siraganian, *J. Immun.* 163:2508-2516, 1999).

ZAP-70 associates with the zeta (t) subunit of the T-cell antigen receptor (TCR) (Chan et al., *Cell* 71:649-662, 1992). It undergoes tyrosine phosphorylation and is essential in mediating signal transduction following TCR stimulation. Similarly, Syk is essential in mediating B-cell responses to antigen.

It has been reported that ZAP-70 phosphorylation activity is reduced or undetectable in malignant cells of cutaneous T-cell lymphoma (Fargnoli et al., *Leukemia* 11(8)1338-1346, 1997). ZAP-70 is not known to be expressed in B-cells.

Provided herein is the identification of ZAP-70 RNA expression levels as a prognostic marker of CLL; this has been reported in Rosenwald et al., *J. Exp. Med.* 194:1639-1647, 2001. Also provided herein is the identification of ZAP-70 protein levels as a prognostic marker of CLL. Based on mRNA and protein expression levels in samples from patients suffering CLL, ZAP-70 has been identified as a molecule that can be used in the clinical classification of patients with CLL/SLL.

V. ZAP-70 Expression to Guide Therapy in CLL

Currently, there is no curative treatment for CLL/SLL and therapy is delayed for as long as possible (NCI trial lists, *JNCI* 1999). Only when clinical symptoms become severe enough is treatment initiated. With the advent of newer therapies it might be beneficial to start treatment before symptoms appear if there was a reliable method to identify patients who would have early disease progression and a more aggressive clinical course (Byrd, *Sem in Oncol*, 1998). ZAP-70 may be able to guide such a strategy of risk adapted treatment. Specifically ZAP-70 negative patients might best be managed by a watch and wait strategy and would be spared potentially harmful treatment. On the other hand, ZAP-70 positive patients might benefit from early intervention before a large tumor bulk accumulates and the patients are weakened by progressive disease. Furthermore, because ZAP-70 expression characterizes CLL cells with a distinct biology it may be possible to select patients for targeted therapeutic strategies based on ZAP-70 expression.

VI. A Role for Zap-70 in the Pathogenesis of CLL/SLL

ZAP-70 is a tyrosine kinase, which associates with the T cell receptor and plays a pivotal role in T cell activation and development. Overexpression or constitutive activation of tyrosine kinases has been demonstrated to be critically involved in a number of malignancies including leukemias and several types of solid tumors. Thus, the detection of ZAP-70 protein expression in CLL/SLL cells raises the question of a pathogenetic role of this kinase in the development or propagation of CLL/SLL. Given the relatively slow growth rate of CLL cells it is not surprising that evidence has not been detected for a constitutive activation of the ZAP-70 kinase in CLL blood cells. However, it is conceivable that activation of ZAP-70 occurs in the bone marrow or lymphatic organs. CLL cells receive survival signals from stromal cells in the microenvironment of these sites. Similarly, microarray data indicate that CLL cells receive important activation signals through the antigen receptor.

The presence of ZAP-70 might affect sensitivity to, duration and/or intensity of such signals and could thus be a key factor for the more aggressive form of CLL. Therefore, targeting ZAP-70 in CLL patients could benefit especially the patients with the more rapidly progressive form of the disease. Because of the important role of ZAP-70 in T-cell signaling, interest in inhibitors targeting ZAP-70 has been high and several candidate drugs have been designed and found to inhibit ZAP-70 function in preclinical models (Nishikawa, *Mol Cell* 2000). The clinical focus of such drugs has been perceived to be immunosuppression. However, as outlined above ZAP-70 might be a promising target for anti-leukemic therapy in CLL. Furthermore, drugs targeting ZAP-70 might have activity in lymphomas, given that ZAP-70 expression was detected in several lymphoma cell lines. Further studies to elucidate these interactions will include functional studies, the use of inhibitors to analyze changes in gene expression profile and the analysis of gene expression in CLL cells under different physiologic conditions.

ZAP-70 will find immediate use as a prognostic marker in CLL/SLL and will be helpful to guide treatment strategies. Even more intriguing is its potential role in disease pathogenesis and progression and the possibility that inhibitors of ZAP-70 may lead to targeted therapy of CLL.

The following examples are provided to illustrate certain particular features and/or embodiments. These examples should not be construed to limit the invention to the particular features or embodiments described.

EXAMPLES

Example 1

Gene Expression Profiling of B Cell Chronic Lymphocytic Leukemia

The most common human leukemia is B cell chronic lymphocytic leukemia (CLL), a malignancy of mature B cells with a characteristic clinical presentation but a variable clinical course. The rearranged immunoglobulin (Ig) genes of CLL cells may be either germ-line in sequence or somatically mutated. Lack of Ig mutations (UM-CLL) defined a distinctly worse prognostic group of CLL patients raising the possibility that CLL comprises two distinct diseases.

Using genomic-scale gene expression profiling, it is demonstrated that CLL is characterized by a common gene expression "signature," irrespective of Ig mutational status, suggesting that CLL cases share a common mechanism of transformation and/or cell of origin. Nonetheless, the expression of hundreds of other genes correlated with the Ig mutational status, including many genes that are modulated in expression during mitogenic B cell receptor signaling. These genes were used to build a CLL subtype predictor for use in the clinical classification of patients with this disease.

The observation that the rearranged Ig variable genes in CLL cells are either unmutated (UM-CLL) or mutated (M-CLL) indicated that CLL can comprise two different diseases lumped together using standard diagnostic methods. Somatic hypermutation of Ig genes is a specialized diversification mechanism that is activated in B cells at the germinal center stage of differentiation. Thus, it was indicated that CLL includes two disparate malignancies, one derived from an Ig-unmutated, pregerminal center B cell, and the other from an Ig-mutated B cell that has passed through the germinal center. This "two disease" model of CLL was further supported by the observation that Ig-unmutated and Ig-mutated CLL patients had distinctly different clinical courses.

One model indicates that Ig-unmutated and Ig-mutated CLL are not highly related to each other in gene expression. A precedent for this model is found in the recent demonstration that another lymphoid malignancy, diffuse large B cell lymphoma (DLBCL), actually includes two distinct diseases that are morphologically indistinguishable but which have largely nonoverlapping gene expression profiles. Alternatively, all cases of CLL can have a common cellular origin and/or a common mechanism of malignant transformation. Thus, in this model, Ig-mutated and Ig-unmutated CLL cases share a gene expression signature that is characteristic of CLL.

To demonstrate these two models, and to identify molecular differences between CLL patients that might influence their clinical course, the gene expression phenotype of CLL on a genomic scale was determined using Lymphochip cDNA microarrays (Alizadeh et al., *Nature* 403:503-511, 2000; Alizadeh et al., *Cold Spring Harbor Symp. Quant. Biol.* 64:71-78, 1999). The data demonstrate that CLL, irrespective of the Ig mutational status, is defined by a characteristic gene expression signature, thus favoring the notion that all cases share some aspects of pathogenesis. Nonetheless, hundreds of genes were found to be differentially expressed between Ig-unmutated and Ig-mutated CLL, providing the first molecular insight into the biological mechanisms that lead to the divergent clinical behaviors of these subgroups of CLL patients. The unexpected finding that B cell activation genes were differentially expressed between the two Ig-mutational subgroups in CLL indicates that signaling pathways downstream of the B cell receptor (BCR) contribute to the more aggressive clinical behavior of the Ig-unmutated subtype.

Methods and Materials

Microarray Procedures.

Peripheral blood samples from CLL patients diagnosed according to National Cancer Institute guidelines (Cheson et al., *Blood* 87:4990-4997, 1996) were obtained after informed consent and were treated anonymously during microarray analysis. Thirty-three CLL patients studied had not received chemotherapy at the time of sample acquisition and four patients had received prior treatment. Ig mutational status was only studied in untreated patients. Leukemic cells from CLL blood samples were purified by magnetic selection for CD19+ (Miltenyi Biotec) at 4° C. before mRNA extraction and microarray analysis. Other mRNA samples from normal and malignant lymphoid populations have been described previously, as have cell purification methods and array methods (Alizadeh et al., *Nature* 403:503-511, 2000). All microarray experiments used the Cy5 dye to generate the experimental cDNA probe from mRNA of normal and malignant lymphocytes, and the Cy3 dye to generate the reference cDNA probe from mRNA pooled from nine lymphoma cell lines as described previously (Alizadeh et al., *Nature* 403: 503-511, 2000).

Initial microarray data selection was based on fluorescence signal intensity. Each selected data point either had 100 relative fluorescent units (RFU's) above background in both the Cy3 and Cy5 channels, or 500 RFU's above background in either channel alone. A supervised selection of genes preferentially expressed in CLL cells was performed as follows. First, it was determined that the majority of cell lines that were used to construct the reference pool of mRNA were derived from DLBCL. The percentage of CLL samples with expression ratio >3 relative to the reference cell line pool was calculated, and the same calculation was also performed for the DLBCL samples. Genes were selected for which >50% of the CLL samples, and <25% of the DLBCL samples, had ratios >3. Additionally, genes were selected if the average CLL ratio was greater than the average DLBCL ratio by greater than threefold. Representative genes were chosen by computing the average expression in CLL samples and the average expression in resting B cell samples (adult and cord blood B cells). CLL signature genes were chosen to be at least twofold more highly expressed in CLL than in resting B cells and CLL/resting B cell genes were chosen to be expressed equivalently (within twofold) in the two sample sets. Duplicate array elements representing the same genes were removed. Germinal center genes were chosen from a previous analysis (Alizadeh et al., *Nature* 403:503-511, 2000).

RT-PCR.

500 ng poly-A+mRNA was used to generate first strand cDNA using Superscript® reverse transcriptase (Life Technologies) together with random hexamers and oligo-dT primers. ZAP-70 oligonucleotide primers (5' TCTCCAAAG-CACTGGGTG 3', SEQ ID NO: 3; 5' AGCTGTGTGTGGAGACAACCAAG 3', SEQ ID NO: 4) were then used for PCR amplification for 27 cycles.

Statistical Analysis.

A two-group t-statistic on log 2 expression ratios was used to measure the ability of each array element to discriminate between the two CLL mutational subtypes univariately. For multivariate subtype prediction, a linear combination of log 2 expression ratios for array elements that were significant at the P<0.001 significance level were used in the univariate analysis. The expression ratios were weighted in the linear combination by the univariate t statistics. The linear combination was computed for each sample and the average linear combination was computed for each CLL subtype. The midpoint of the two CLL subtype means was used as a cut-point for subtype prediction. For the cross-validation analysis, the subtype predictor was calculated by sequentially omitting one sample from the test set of cases, and using the remaining cases to generate the predictor. Calculation of the P value from the permutation distribution of the t-statistic also demonstrated the high statistical significance of the differential gene expression between the CLL subtypes. Classification was determined on all CLL cases with the exception of CLL-60 (Ig-unmutated) and CLL-21 and CLL-51 (minimally mutated cases).

The choice of B cell activation genes was made as follows. The B cell activation series of microarray experiments included several different stimulations with anti-IgM for 6, 24, and 48 hours for each Lymphochip array element, the data were averaged at each activation time point, and then selected those elements that gave a twofold induction compared with the resting B cell average for at least one time point.

Results

The Gene Expression Signature of CLL.

Gene expression in CLL samples (n=37) was profiled using Lymphochip cDNA microarrays containing 17,856 human cDNAs (Alizadeh et al., *Cold Spring Harbor Symp. Quant. Biol.* 64:71-78, 1999). To facilitate comparison of each CLL mRNA sample with the others and with previously generated data sets, gene expression in each CLL mRNA sample was compared to a common reference mRNA pool prepared from lymphoid cell lines (Alizadeh et al., *Nature* 403:503-511, 2000; Alizadeh et al., *Cold Spring Harbor Symp. Quant. Biol.* 64:71-78, 1999). Using this strategy, the relative gene expression in the CLL cases could be compared with other B cell malignancies (DLBCL and follicular lymphoma) and of normal B cell and T cell sub-populations. Expression data from 328 Lymphochip array elements representing 247 genes that were selected in a supervised fashion (see Materials and Methods) to be more highly expressed in the majority of CLL samples than in DLBCL samples (n=40) were obtained. These genes fall into two broad categories. Genes in the first category define a CLL gene expression "signature" that distinguishes CLL from various normal B cell subsets and from other B cell malignancies. The CLL signature genes were not expressed highly in resting blood B cells or in germinal center B cells. This group of genes includes several genes not previously suspected to be expressed in CLL (e.g., Wnt3, titin, Ror1) as well as a number of novel genes from various normal and malignant B cell cDNA libraries. By contrast, CLL cells lacked expression of most genes that are preferentially expressed in germinal center B cells. In addition to this set of CLL signature genes, CLL preferentially expressed a set of genes that distinguish resting, G0 stage blood B cells from mitogenically activated blood B cells and germinal center B cells that are traversing the cell cycle. The expression of these resting B cell genes by CLL cells is consistent with the indolent, slowly proliferating character of this malignancy.

One of these resting B cell samples was prepared from human umbilical cord blood that is enriched for B cells bearing the CD5 surface marker, a B cell subpopulation that has been proposed to be the normal counterpart of CLL. The cord blood B cells were >80% CD5$^+$ by FACS® flow cytometry analysis whereas resting B cells from adult blood are 10-20% CD5$^+$ (Geiger et al., *Eur. J. Immunol.*, 30:2918, 2000). Notably higher expression of the CLL signature genes in the cord blood B cell sample than in the adult B cell sample was not observed, and no overall correlation in the expression of genes was observed between CLL and either adult or cord blood B cells (Pearson correlation coefficients –0.27 and –0.21, respectively). Thus, the gene expression profiling analysis does not provide support for the hypothesis that the CD5$^+$ B cell is a CLL precursor. However, that the expression of the CLL signature genes can be due to the oncogenic mechanisms of CLL and therefore is not a feature of any normal B cell subpopulation.

Ig Mutational Status.

The expressed Ig heavy chain genes were sequenced from 28 CLL cases and compared with known germ-line encoded Ig VH segments as described previously (Bessudo et al., *Blood* 88:252-260, 1996). By convention, VH sequences that matched known germ line sequences with >98% identity were considered unmutated, as any minor differences observed in this group were assumed to reflect genetic polymorphism (Fais et al., *J. Clin. Invest.* 102:1515-1525, 1998; Hamblin et al., *Blood* 94:1848-1854, 1999; Damle et al., *Blood* 94:1840-1847, 1999). By this criterion, 16 CLL cases in the study set were unmutated. The remaining cases were further separated into a group of 10 highly mutated cases (<97% identity with any germ-line VH segment) and a group of two cases that were minimally mutated (>97% but <98% identity with known germ-line VH genes). CLL cases were grouped according to Ig mutational status as indicated above. Although some variation in expression of the CLL signature and CLL/resting B cell genes was evident between CLL patients, most patients in each Ig mutational subtype highly expressed these genes at comparable levels. Furthermore, an unsupervised hierarchical clustering of the CLL cases using 10,249 Lymphochip array elements resulted in a clustering dendrogram in which the Ig-unmutated and Ig-mutated CLL cases were extensively intermingled. Thus, the overall gene expression profiles of the two CLL subtypes were largely overlapping.

Segregation of the patients according to Ig mutational status revealed that Ig-unmutated CLL patients had a significantly worse clinical course, requiring earlier treatment, than the Ig-mutated CLL patients, in keeping with previous reports (Hamblin et al., *Blood* 94:1848-1854, 1999; Damle et al., *Blood* 94:1840-1847, 1999).

CLL Subtype Distinction Genes.

Given the dramatically different clinical behavior of the Ig-unmutated and Ig-mutated CLL patients, gene expression differences can be discerned between these groups. To both demonstrate such genes and statistically validate their relationship to the Ig-mutational subgroups, the Ig mutational analysis was conducted independently and sequentially in two random subsets of the CLL patients (FIG. 1). The "training" set consisted of ten Ig-unmutated cases and eight Ig-mutated cases. In this gene discovery phase, the minimally mutated CLL cases were assigned to the mutated class. The mean expression of each gene was then calculated for both mutational subgroups and the statistical significance of the difference of these means was determined. All genes that discriminated between the mutational subgroups at a significance of P<0.001 (n=56) were used to form a "predictor" that could be used to assign a CLL sample to a mutational subgroup based on gene expression (see Methods).

The performance of this CLL subtype predictor was initially demonstrated using a cross-validation strategy (FIG. 1A). One of the 18 CLL samples in the training set was omitted, the statistically significant genes were determined, and a predictor was calculated based on the remaining 17 samples. The omitted sample was then assigned to a CLL subtype based on gene expression using this predictor. The Ig mutational status of 17 CLL samples was correctly assigned by this procedure with one misassignment. To determine the statistical significance of this result, 1,000 random permutations of the assignments of CLL samples to the Ig mutation subgroups were created. For each permutation, the cross-validation process described above was repeated. Only one of the 1,000 random permutations generated a predictor that performed as well as the predictor based on the unpermuted data, demonstrating that the significance of the gene expression difference between the CLL subtypes was P=0.001.

Figure 1B:
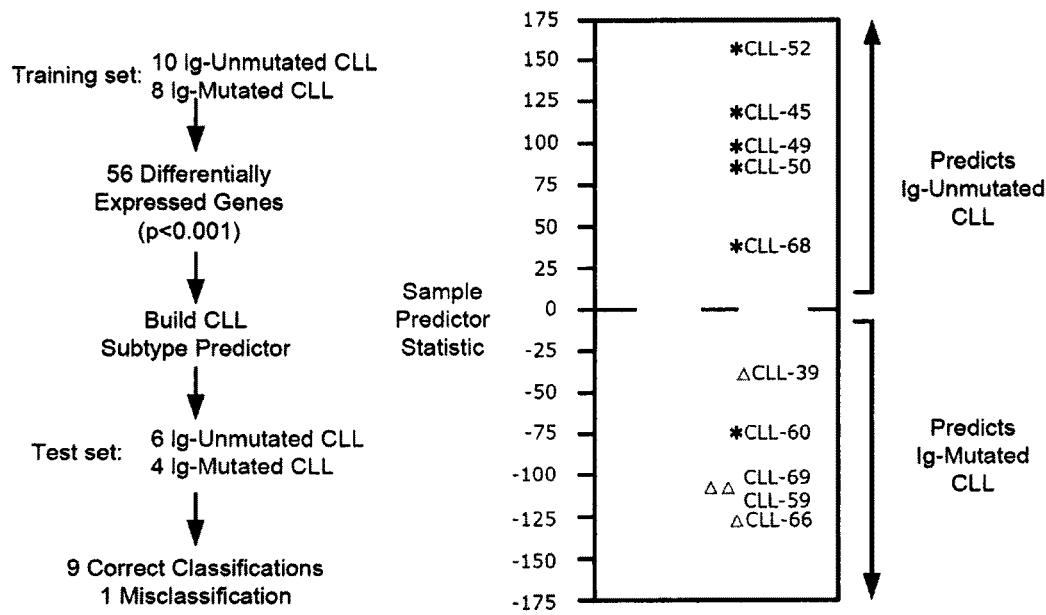
FIG. 1B shows the performance of the Ig-mutational subtype predictor in a test set of six unmutated (*) and four mutated CLL (Δ) samples.

Finally, the Ig mutational status of a "test" set of 10 additional CLL cases was determined and the predictor derived from the training set was used to assign the cases in this test set to a CLL subtype based on gene expression in a blinded fashion (FIG. 1B). Nine out of ten of the test cases were correctly assigned, showing the ability of the CLL subtype predictor to correctly assign new CLL cases based on gene expression data that was not used to generate the predictor. The one misclassified CLL case (CLL-60) clearly was an outlier in gene expression. Taken together with the cross-validation results, these data demonstrate that gene expression can define CLL subtypes that have different degrees of Ig mutation.

These findings can be used to create a diagnostic test for the CLL subtypes based upon gene expression. In this regard, one of the most differentially expressed genes from the analysis of the training set of cases, ZAP-70, could classify all of the cases in both the training and the test set with 100% accuracy. Likewise, predictors based on two genes (ZAP-70 and IM1286077) or three genes (ZAP-70, IM1286077, activation-induced C-type lectin) discovered using the training set formed CLL subtype predictors that performed with 100% accuracy on the training set and test set of CLL cases.

The search for CLL subtype distinction genes was next expanded using data from both the training set and test set of CLL cases. The two CLL cases with minimal Ig mutations (CLL-22 and CLL-51) were excluded based on the possibility that their Ig sequences might actually represent as yet undescribed polymorphic VH alleles. CLL-60 was excluded based on its unusual gene expression characteristics that led to its misclassification by the CLL subtype predictor. Two hundred and five Lymphochip array elements (175 genes) that were differentially expressed between the CLL subtypes had a statistical significance of P<0.001. Hierarchical clustering of the CLL cases based on expression of these genes placed the majority of Ig-unmutated CLL cases in one cluster and the Ig-highly mutated CLL cases in another. As expected, CLL-60 was more closely aligned with the Ig-mutated CLL cases, though it was an outlier from the major cluster of Ig-mutated CLL cases. Interestingly, both of the CLL cases with a low Ig mutational load were also outliers, though they were more closely related to the Ig-mutated CLL subtype than to the Ig-unmutated CLL subtype. These data define two predominant CLL subtypes that differ in the expression of hundreds of genes but also demonstrate that additional minor CLL subtypes may exist that have distinct gene expression profiles. ZAP-70 was the most tightly discriminating gene, with an average 4.3-fold higher expression in Ig-unmutated CLL than in Ig-mutated CLL (P<10-6). RT-PCR analysis confirmed ZAP-70 expression in two Ig-unmutated CLL cases (CLL-48 and CLL-49), in contrast to CLL-66 and CLL-69 that were Ig-mutated. Surprisingly, ZAP-70 expression was also observed in several B cell lines (LILA, LK-6, OCI-Ly2).

Relationship Between B Cell Activation and the CLL Subtype Distinction.

Several of the CLL subtype distinction genes are known or suspected to be induced by protein kinase C (PKC) signaling, including activation-induced C-type lectin (Hamann et al., *Immunogenetics*, 45:295, 1997), MDS019, a very close paralogue of phorbolin 1 (Madsen et al., *J. Invest. Dermatol.* 113:162-169, 1999), and gravin, a scaffold protein that binds PKC and may regulate its activity (Nauert et al., *Curr. Biol.* 7:52-62, 1997). One mechanism by which PKC is activated in B cells is through BCR signaling (Cambier et al., *Annu. Rev. Immunol.* 12:457-486, 1994). Therefore, it was determined whether the CLL subtype distinction genes are regulated during activation of blood B cells, using a gene expression database generated previously using Lymphochip microarrays (Alizadeh et al., *Nature* 403:503-511, 2000). Strikingly, many of the genes that were more highly expressed in Ig-unmutated CLL were induced during activation of blood B cells. Many of these genes encode proteins involved in cell cycle control (e.g., cyclin D2) or in cellular metabolism required for cell cycle progression (e.g., HPRT and other nucleotide modifying enzymes). Conversely, the majority of the genes that were expressed at lower levels in Ig-unmutated CLL were strongly down-modulated during B cell activation. These results demonstrate that the CLL subtype distinction genes are enriched for genes that are modulated in expression by B cell activation. Indeed, 47% of the CLL subtype distinction genes were induced during B cell activation, whereas only 18% of all Lymphochip genes were in this category.

Gene Expression in CLL Provides New Understanding of the Etiology of CLL and the Divergent Clinical Courses of Patients Suffering from CLL.

Using genomic-scale gene expression profiling, a current controversy in CLL pathogenesis, namely whether this diagnosis comprises more than one disease entity, was addressed. CLL patients have been subdivided based on the Ig mutational status of their leukemic cells (Fais et al., *J. Clin. Invest.* 102:1515-1525, 1998; Hamblin et al., *Blood* 94:1848-1854, 1999; Damle et al., *Blood* 94:1840-1847, 1999), but it was unclear whether these patients had molecularly distinct diseases. The data demonstrate that all CLL patients share a characteristic gene expression signature in their leukemic cells.

These findings support a model in which all cases of CLL have a common cell of origin and/or a common mechanism of malignant transformation. In this model, the CLL-specific gene expression signature might represent the gene expression signature of a common normal precursor cell or it might reflect the downstream gene expression consequences of a common oncogenic event. These findings are in contrast to the previous observation that DLBCL consists of two disease entities that did not have overlapping gene expression outside of genes involved in proliferation and in the host response to the tumor (Alizadeh et al., *Nature* 403:503-511, 2000).

CLL cells proliferate slowly in vivo, driven by unknown signals. Therefore, it is notable that Wnt-3 was highly, and selectively, expressed in CLL. The Wnt gene family encodes secreted proteins that signal through cell surface receptors of the frizzled family to control development and mediate malignant transformation (Polakis, *Genes Dev.* 14:1837-1851, 2000). Intriguingly, another CLL signature gene, Ror1, encodes a receptor tyrosine kinase with an extracellular domain that resembles a Wnt interaction domain of frizzled (Saldanha et al., *Protein Sci.* 7:1632-1635, 1998). Recently, Wnt-3 has been shown to promote proliferation of mouse bone marrow pro-B cells by initiating signaling events leading to transcriptional activation by LEF-1 (Reya et al., *Immunity* 13:15-24, 2000). Thus, CLL cells can use an autocrine mechanism of proliferation that is used normally by B cell progenitors.

It was nevertheless also found that the expression of hundreds of other genes correlated with the Ig mutational status in CLL, providing insights into the biological mechanisms that lead to the divergent clinical behaviors of CLL patients. The most differentially expressed gene between the CLL subtypes was ZAP-70, a kinase that transduces signals from the T cell antigen receptor, and is preferentially expressed in normal T lymphocytes (Chu et al., *Immunol. Rev.* 165:167-180, 1998). Differential expression of ZAP-70 between CLL subtypes was therefore surprising, since its expression in normal B cells has not been previously reported. However, by microarray analysis and RT-PCR analysis it was found that ZAP-70 mRNA is highly expressed in some B lymphoma cell lines along with being differentially expressed by the CLL subtypes. A ZAP-70-related kinase, syk, transduces signals from the B cell receptor (BCR) (Turner et al., *Immunol. Today* 21:148-154, 2000), raising the possibility that ZAP-70 might alter BCR signaling in CLL cells.

Another CLL subtype distinction gene, Pak1, could contribute to the resistance of CLL cells to apoptosis by phosphorylating Bad and thereby preventing Bad from inhibiting BCL-2 (Schurmann et al., *Mol. Cell. Biol.* 20:453-461, 2000). Fibroblast growth factor receptor (FGFR) 1 is a receptor tyrosine kinase that can stimulate cellular proliferation after interaction with fibroblast growth factors. The higher expression of FGFR1 in Ig-unmutated CLL is intriguing given that CLL patients have elevated blood levels of basic fibroblast growth factor, which can activate FGFR1 and block apoptosis in CLL (Aguayo et al., *Blood* 96:2240-2245, 2000; Menzel et al., *Blood* 87:1056-1063, 1996).

Intriguingly, CLL subtype distinction genes were enriched for genes that are modulated in expression during signaling of B cells through the BCR. One hypothesis raised by this observation is that the leukemic cells in Ig-unmutated CLL may have ongoing BCR signaling. Interestingly, the VH repertoire usage in the Ig-unmutated and Ig-mutated CLL is distinct (Fais et al., *J. Clin. Invest.* 102:1515-1525, 1998; Hamblin et al., *Blood* 94:1848-1854, 1999; Damle et al., *Blood* 94:1840-1847, 1999) and the combinations of VH, DH, and JH gene segments rearranged in CLL cells are not random (Fais et al., *J. Clin. Invest.* 102:1515-1525, 1998; Hamblin et al., *Blood* 94:1848-1854, 1999; Damle et al., *Blood* 94:1840-1847, 1999; Widhopf and Kipps, *J. Immunol.* 166:95-102, 2001; Johnson et al., *J. Immunol.* 158:235-246, 1997). These observations suggest that the surface Ig receptors of CLL cells may have specificity for unknown environmental or self-antigens. Indeed, CLL cells have been shown to frequently produce antibodies that bind classical autoantigens (Borche et al., *Blood* 76:562-569, 1990; Sthoeger et al., *J. Exp. Med.* 169: 255-268, 1989; Broker et al., *J. Autoimmun.* 1:469-481, 1988). The gene expression profiling data presented herein indicate that Ig-unmutated CLL cells is continuously stimulated in vivo by antigen, giving rise to a gene expression profile that is consistent with BCR signaling. Indeed, CLL cells from patients with progressive disease were more readily stimulated by BCR cross-linking to synthesize DNA than were CLL cells from patients with stable disease (Aguilar-Santelises et al., *Leukemia* 8:1146-1152, 1994). Although this study did not distinguish between Ig-unmutated and Ig-mutated CLL, the results are consistent with a differential ability of these subtypes to signal through the BCR. Alternatively, Ig-unmutated CLL cells can activate the same signaling pathways that are engaged during B cell activation as a result of genetic changes in the leukemic cells or by other pathological mechanisms.

An immediate clinical application of these results is the differential molecular diagnosis of CLL. It was demonstrated that as few as 1-3 genes could correctly assign patients to a CLL subtype with 100% accuracy. Thus, the results can be used to establish a variety of prognostic tests. Examples of such tests include RNA- and DNA-based techniques such as microarrays or PCR. A prognostic test, such as a quantitative RT-PCR test to diagnose the CLL subtypes, would be easier to adopt clinically than DNA sequence analysis of Ig variable regions. Given the relatively benign course of Ig-mutated CLL, a simple diagnostic test based on gene expression provides valuable prognostic information for CLL patients and can be used to guide treatment decisions.

In addition, new therapeutic approaches to this currently incurable leukemia are provided herein. First, the protein products of some of the CLL signature genes present new targets for therapeutic agents or drugs. These agents can include kinase inhibitors, antibodies for use in mAb therapy, and molecular decoys that affect protein-protein interactions (for example, antagonists). The protein products may also be of use in vaccine approaches to CLL. Agents that can modify the expression of the protein products of the CLL signature genes include antisense oligonucleotides or small inhibitory RNA. Second, the unexpected finding that B-cell activation genes were upregulated in Ig-unmutated CLL patients indicates that signaling pathways downstream of the BCR contribute to the more progressive clinical course of these patients. Thus, therapeutic targeting of these signaling pathways, using methods such as those described above, will specifically benefit those CLL patients that show gene expression evidence that these pathways are active.

Example 2

ZAP-70 Expression Identifies a CLL/SLL Subtype

Given the clinical differences between Ig-mutated and Ig-unmutated CLL, it would be beneficial to incorporate this distinction into the clinical diagnosis of CLL patients. Most clinical diagnostic laboratories do not have the routine ability to sequence IgVH genes. This analysis is time consuming and expensive, making it doubtful that it can be established as a clinical test available to all CLL patients. Further, the distinction between Ig-mutated and Ig-unmutated CLL is based on the degree of identity between the CLL IgVH sequence and the closest germline IgVH sequence. However, the optimal cut point for this distinction is not clear. Early studies used a cutoff of 98% sequence identity to allow for germline Ig polymorphisms in the human population (Damle et al., *Blood,* 94:1840, 1999; Hamblin et al., *Blood,* 94:1848, 1999; Oscier et al., *Blood,* 89:4153, 1997). In a recent study with 300 patients, a cutoff of 97% sequence identity was optimal for distinguishing CLL patients that had different overall survival rates (Krober et al., *Blood,* 100:1410, 2002). However, the 95% confidence interval for this distinction ranged from 96% to 98% sequence identity.

Expression of CD38, as determined by flow cytometry, has been shown to have prognostic significance in CLL (D'Arena et al., *Leuk. Lymphoma,* 42:109, 2001; Del Poeta et al., *Blood,* 98:2633, 2001' Durig et al., *Leukemia,* 16:30, 2002; Ibrahim et al., *Blood,* 98:181, 2001). Initially, it was proposed that CD38 might serve as a surrogate marker for IgVH mutational status (Damle et al., *Blood,* 94:1840, 1999). Subsequent studies have not always shown this relationship (Hamblin et al., *Blood,* 99:1023, 2002; Thunberg et al., *Blood,* 97:1892, 2001). It has also been suggested that CD38 expression might add to the prognostic information in patients with known IgVH status (Hamblin et al., *Blood,* 99:1023, 2002), but two large studies that together included more than 500 patients failed to confirm CD38 as an independent prognostic factor in multivariate analysis (Krober et al., *Blood,* 100:1410, 2002; Oscier et al., *Blood,* 100:1177, 2002). Some of the differences may be due to technical aspects of the CD38 assays and the choice of an optimal cut point for the number of CD38+ cells. The largest study to date found that a cutoff of 7% was best at separating different prognostic groups (Krober et al., *Blood,* 100:1410, 2002). Another confounding issue is that CD38 expression by the leukemic clone may change during the course of the disease, and an increase of CD38 expression may herald disease progression (Hamblin et al., *Ann. Hematol.,* 81:299, 2002).

Here, in a separate study from that described in Example 1, it is demonstrated how ZAP-70 expression is able to discriminate between clinical subgroups of CLL/SLL. ZAP-70 expression correlates with unmutated immunoglobulin genes and more aggressive disease. Thus, the results of this study confirm and expand the results of the study described in Example 1. Tests were developed to assess ZAP-70 nucleic acid and ZAP-70 protein expression suitable for routine clinical laboratory use. Thus, testing for ZAP-70 expression can be performed in the clinic, to yield important prognostic information and help guide treatment decisions.

Materials and Methods

Patient Samples.

All patients included in this study were enrolled in a clinical protocol at the National Institutes of Health and gave informed consent to the use of blood and tissue samples for research. Peripheral blood mononuclear cells (PBMC) were obtained by FICOLL® copolymer gradient centrifugation (ICN Biomedicals). Leukemic cells were purified by magnetic selection for CD19 expression (Miltenyi Biotech). To obtain paraffin cell pellets, PBMC were washed in PBS, pelleted and resuspended in plasma. Clot formation was initiated with the addition of thrombin. The clot was fixed in formalin and processed by routine techniques. Bone marrow biopsies and aspirate sections were obtained and processed by routine techniques.

Determination of Immunoglobulin Mutational Status.

Five hundred nanograms of mRNA or 1-5 μg of total RNA was used to generated oligo-dT primed cDNA using Superscript® reverse transcriptase (Life Technologies). Amplification of the immunoglobulin V-heavy sequence was performed essentially as described (Hamblin et al., *Blood* 94:1848, 1999; Fais et al., *J. Clin. Invest.,* 102:1515, 1998; Campbell et al., *Mol. Immunol.,* 29:193, 1992). In brief: cDNA was amplified by polymerase chain reaction (PCR) using a mixture of 5' oligonucleotides specific for each leader sequence of the VH1 to VH7 IgVH families as forward primers (VH1 and VH7: 5'-CCA TGG ACT GGA CCT GGA-3' (SEQ ID NO: 5); VH2: 5'-ATG GAC ATA CTT TGT TCC AC-3' (SEQ ID NO: 6); VH3: 5'-CCA TGG AGT TTG GGC TGA GC-3' (SEQ ID NO: 7); VH4: 5'-ATG AAA CAC CTG TGG TTC TT-3' (SEQ ID NO: 8); VH5: 5'-ATG GGG TCA ACC GCC ATC CT-3' (SEQ ID NO: 9); VH6: 5'-ATG TCT GTC TCC TTC CTC AT-3') (SEQ ID NO: 10)) and either a 3' oligonucleotide complementary to the JH consensus sequence (5'-ACC TGA GGA GAC GGT GAC C-3'; SEQ ID NO: 11) or the constant region of the IgM locus (5'-AGG AGA AAG TGA TGG AGT CG-3'; SEQ ID NO: 12) as reverse primers (Campbell et al., *Mol. Immunol.* 29:193, 1992; Fais et al., *J. Clin. Invest.* 102: 1515, 1998). For samples that failed to amplify with this combination, IgVH family specific primers complementary to the 5' end of framework region (FR)1 were used (FR1-VH1: TGC AGC TGG TGC AGT CTG-3' (SEQ ID NO: 16); FR1-VH2: 5'-AGG TCA ACT TAA GGG AGT CTG (SEQ ID NO: 17); FR1-VH3: 5'-AGG TGC AGC TGG TGG AGT CTG-3' (SEQ ID NO: 18); FR1-VH4: 5'-AGG TGC AGC TGC AGG AGT CGG-3' (SEQ ID NO: 19); FR1-VH5: 5'-AGG TGC AGC TGC TGC AGT CTG-3' (SEQ ID NO: 20); FR1-VH6: 5'-AGG TAC AGC TGC AGC AGT CAG-3' (SEQ ID NO: 21); (Marks et al., *Eur. J. Immunol.* 21:985, 1991)).

PCR was performed in 50 μL reactions with Taq polymerase (Sigma) and 20 pmol of each primer. Cycling conditions were 94° C. 30 sec, 60° C. 20 sec, 72° C. 30 sec for up to 35 cycles. Products were purified (MinElute® PCR Purification Kit, Qiagen) and sequenced directly with the appropriate 3' oligonucleotide using BigDye® Terminator reagent and analyzed on an automated DNA sequencer (Applied Biosystems). Nucleotide sequences were aligned to the V-Base sequence directory found on the Medical Research Council Centre for Protein Engineering website. Percentage homology was calculated by counting the number of mutations between the 5' end of FR1 and the 3' end of FR3. Sequences with <2% deviation from the germline VH sequence were considered unmutated (Hamblin et al., Blood 94:1848, 1999).

CD38 Expression Analysis.

Whole blood was stained within 24 hours of Collection with a panel of antibodies as previously described (Fukushima et al., *Cytometry,* 26:243, 1996). Five-parameter, three-color flow cytometry was performed with a FACSCalibur™ flow cytometer and analyzed with CellQuest software (Becton Dickinson). Lymphocytes were gated by forward and side scatter. Isotype controls were run with each patient specimen. CD38 positive cells were determined as the percent of lymphocytes staining more intensely with anti-CD38 (CD38-PE, Becton Dickinson) than with isotype control.

DNA Microarray Analysis.

The DNA microarray methods have been described in detail in Example 1. Fluorescently labeled cDNA probes were generated from mRNA (Fast Track, Invitrogen), using the Cy5 dye to label cDNA from the CLL samples, and the Cy3 dye to label cDNA from a reference pool of mRNA prepared from 9 lymphoma cell lines (Alizadeh et al., *Nature* 403:503, 2000). Lymphochip DNA microarrays containing 13,868 human cDNAs were prepared and used as previously described (see Example 1, Alizadeh et al., *Nature* 403:503, 2000). Initial microarray data selection was based on fluorescence signal intensity, with the requirement of 50 relative fluorescent units (RFU's) above background in both the Cy3 and Cy5 channels, or 500 RFU's above background in either channel alone.

Protein Lysates and Western Blotting.

Twenty million CD19+ purified CLL cells were lysed in 1 mL of lysis buffer containing 1% TRITON® non-ionic surfactant. Protein concentration was determined by Bradford assay. 12 μg of protein per lane was loaded on precast SDS gels (Invitrogen) and separated and transferred to nitrocellulose as recommended by the manufacturer. Western blots were incubated with a mouse monoclonal antibody to ZAP- 70 (clone 2F3.2, Upstate Biotechnology) in PBS with 4% milk. Secondary staining was done with horseradish peroxidase coupled anti mouse antibodies and chemiluminescence (Amersham).

Immunohistochemistry

Immunohistochemistry was performed on deparaffinized sections, taken from neutral buffered formalin-fixed, paraffin-embedded (FFPE) tissue using a panel of monoclonal and polyclonal antibodies (listed below). Bone marrow trephine biopsies were also decalcified prior to sectioning. In brief, the deparaffinized slides were placed in a microwaveable pressure cooker containing 1.5 liters of 10 mM citrate buffer (pH of 6.0) containing 0.1% TWEEN® 20 detergent, and microwaved (Model R4A80, Sharp Electronics, Rahway, N.J.) for 40 min at 700 watts. Antigens were localized using an avidin-biotin-peroxidase method with 3,3'-diaminobenzidine as a chromogen and performed using an automated immunostainer (Ventana Medical Systems, Inc., Tucson, Ariz.) according to the manufacturer's protocol with minor modifications. Primary antibody incubation was performed for 2 hours. Positive and negative controls were run with all cases and stained appropriately. Anti-CD3 and anti-CD20 antibodies were obtained from Dako (Carpenteria, Calif.). An independent pathologist scored all slides in a blinded fashion.

TABLE 1

Antibodies and conditions used for immunohistochemistry.

| Antigen | Clone | Dilution | Source |
|---|---|---|---|
| ZAP-70 | 2F3.2 | 1:80 | Upstate Biotechnology (Lake Placid, NY) |
| ZAP-70 | Polyclonal (sc-574) | 1:20 | Santa Cruz Biotechnology (Santa Cruz, CA) |
| ZAP-70 | mouse monoclonal | 1:100 | BD Transduction Laboratories (Lexington, KY) |
| CD3 | Polyclonal | 1:100 | Dako (Carpinteria, CA) |
| CD5 | 4C7 | 1:50 | Novocastra (Newcastle Upon Tyne, England) |
| CD20 | L26 | 1:200 | Dako |

Flow Cytometry.

Cell lines or ficolled PBMCs were fixed and permeabilized using commercially available kits (Fix and Perm, Caltag; Intrastain, Dako) stained with 0.2-1 µg of primary antibody against ZAP-70 (Upstate Biotechnology) and PE labeled secondary rat anti mouse antibody (Becton Dickinson). Cells were analyzed on a FACSort™ flow cytometer (Becton Dickinson).

Statistical Analysis.

A two-group t-statistic on log 2-transformed mRNA expression ratios was used to measure the ability of each array element to discriminate between the two IgVH mutation subtypes of CLL univariately. To create a test for this subtype distinction based on ZAP-70 mRNA expression, the patients were divided into two groups based on a cut point of ZAP-70 expression that minimized the classification errors. Time to treatment measured from diagnosis was estimated by the Kaplan-Meier method and compared by the log-rank test.

Quantitative RT-PCR.

An aliquot of the same mRNA used for the DNA microarray study was diluted to approximately 0.5 ng/µL. Five µL of the diluted mRNA per reaction was used for quantitative RT-PCR using TaqMan™ reagents and analyzed in real time on an ABI Prism 7700 Sequence Detector as recommended by the manufacturer (Applied Biosystems). All samples were run in triplicates. Amplification of the sequence of interest was compared to a reference probe (β-2-microglobulin) and normalized against a standard curve of Jurkat cell mRNA. Primers and probes for β-2-microglobulin and Cyclin D1 have been described (Bijwaard et al., Clin. Chem. 47:195, 2001) and for ZAP-70 these were 5'-CGCTGCACAAGTTC-CTGGT-3' (forward primer, SEQ ID NO: 13), 5'-GACAC-CTGGTGCAGCAGCT-3' (reverse primer, SEQ ID NO: 14) and 5'-CATTGCTCACAGGGATCTCCTCCCTCT-3' (FAM™-probe, SEQ ID NO: 15).

Results

CLL Subtype Distinction Genes.

In this study, Lymphochip DNA microarrays were used to profile gene expression in CD19+ purified CLL samples from a cohort of 39 patients in order to identify the genes that most accurately discriminate between the CLL subtypes, which could potentially be used in a clinical test for this distinction. Using a conventional cutoff of 98% sequence identity to the nearest germline IgVH sequence, 28 cases (72%) were classified as Ig-mutated CLL and 11 cases (28%) were classified as Ig-unmutated CLL. Of the Ig-unmutated CLL samples, seven (64%) were 100% identical to a germline IgVH sequence and four (36%) were 98-99% identical. The Ig-unmutated and Ig-mutated CLL samples differentially expressed ~240 genes (304 microarray elements) with high statistical significance (p<0.001). These differentially expressed genes included many that were identified in pilot gene expression profiling studies of CLL (see Example 1, above; Klein et al., J. Exp. Med. 194:1625, 2001). ZAP-70 was by far the best subgroup distinction gene in the present analysis. ZAP-70 expression was, on average, 5.54 fold higher in Ig-unmutated CLL than in Ig-mutated CLL and distinguished the subtypes with a statistical significance of $p<10^{-21}$.

ZAP-70 and CD38 as Surrogate Markers of IgVH Mutation Status.

Figure 2:
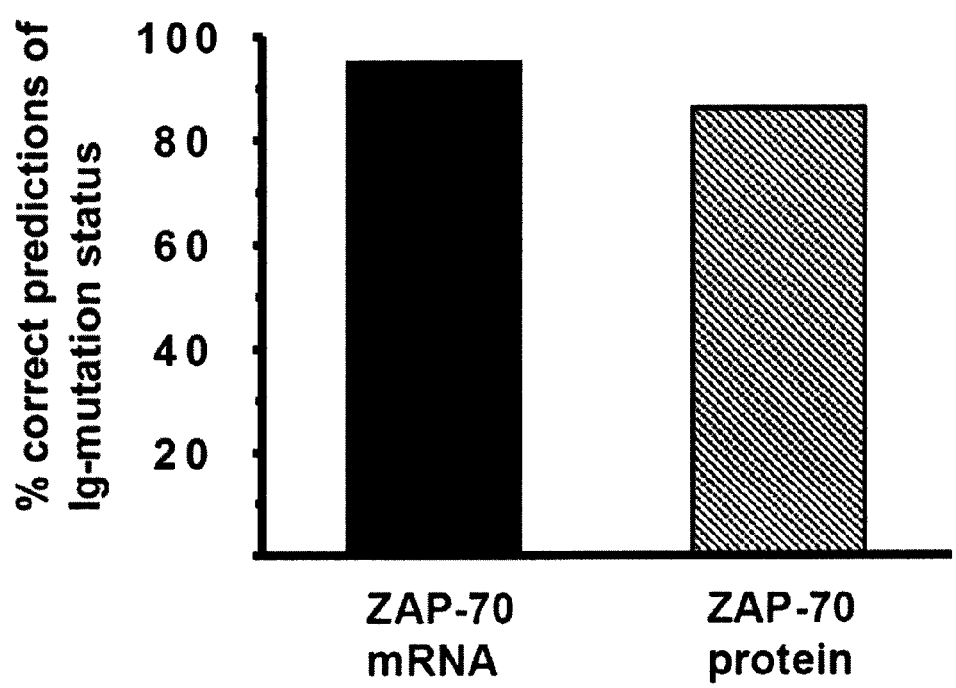
FIG. 2 is a graph showing the predictive value of ZAP-70 mRNA and protein expression as surrogate markers of IgVH mutation status in CLL. ZAP-70 mRNA expression levels, as determined by DNA microarray analysis, predicted Ig-mutation status correctly in 95% of patients. ZAP-70 protein expression as determined by immunohistochemistry predicted Ig-mutation status correctly in 86% of patients.

IgVH mutation status confers important prognostic information, but IgVH sequencing is not suitable for most clinical laboratories. It was therefore investigated whether ZAP-70 mRNA expression could be used as a surrogate marker for this distinction. To do this, a cut point was determined based on ZAP-70 expression levels that would optimally distinguish most Ig-unmutated CLL samples from most Ig-mutated CLL samples. Using this cut point, 95% of the CLL samples could be classified into the correct CLL subtype (FIG. 2). Two samples (5%) were discordant for IgVH mutation status and ZAP-70 expression. Among the 281 g-mutated CLL samples, two showed ZAP-70 expression levels comparable to Ig-unmutated CLL. Other genes, were searched for that had expression patterns that could be combined with ZAP-70 expression to create a multivariate classifier that would perform better than ZAP-70 expression alone. No such gene was found.

CD38 surface expression has been shown to be a surrogate marker of IgVH mutation status in some studies (Damle et al., Blood, 94:1840, 1999). Flow cytometric analysis of CD38 expression was available on 36 patients in this study. Early studies considered CLL cases with ≥30% CD38-expressing cells to be CD38+ (Damle et al., Blood, 99:4087, 2002). Based on this criterion, 11 (31%) of our CLL samples were CD38+. More recently, CD38+ CLL cases were defined as those with ≥7% CD38-expressing cells, based on overall survival analysis in 200 patients (Krober et al., Blood, 100: 1410, 2002). In the present series, 14 patients (39%) were CD38+ by this criterion. As expected, CD38 expression tended to be higher in Ig-unmutated CLL samples, but there was a considerable overlap in CD38 expression between the CLL subtypes. Overall, CD38 predicted IgVH mutation status correctly in 86% of patients when a cutoff of 30% was used and in 78% when a cutoff of 7% was applied. Thus, considerably more patients were misclassified by CD38 expression than by ZAP-70 expression. Furthermore, CD38 expression yielded more false positive (27%) and false negative (8%) assignments than did ZAP-70 expression (15% and 0%, respectively).

Figure 3A:
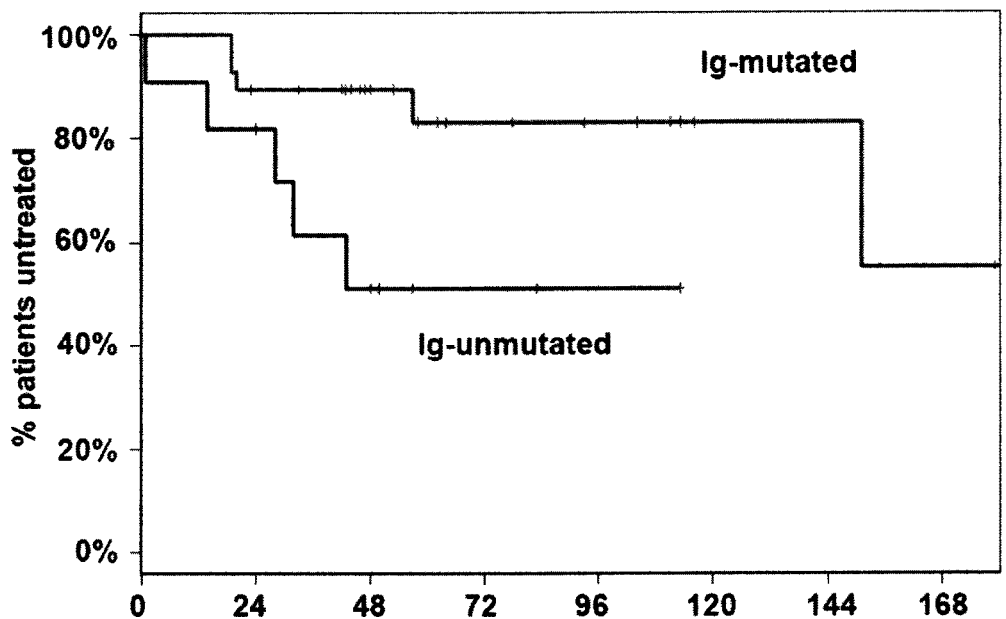
FIGS. 3A and B is a series of graphs showing the impact of ZAP-70 mRNA and Ig-mutation status on the clinical course of CLL. Rate of disease progression is shown, as assessed by the treatment-free time interval measured in months from diagnosis for IgVH mutation status (FIG. 3A) and ZAP-70 mRNA expression (FIG. 3B).
Figure 3B:
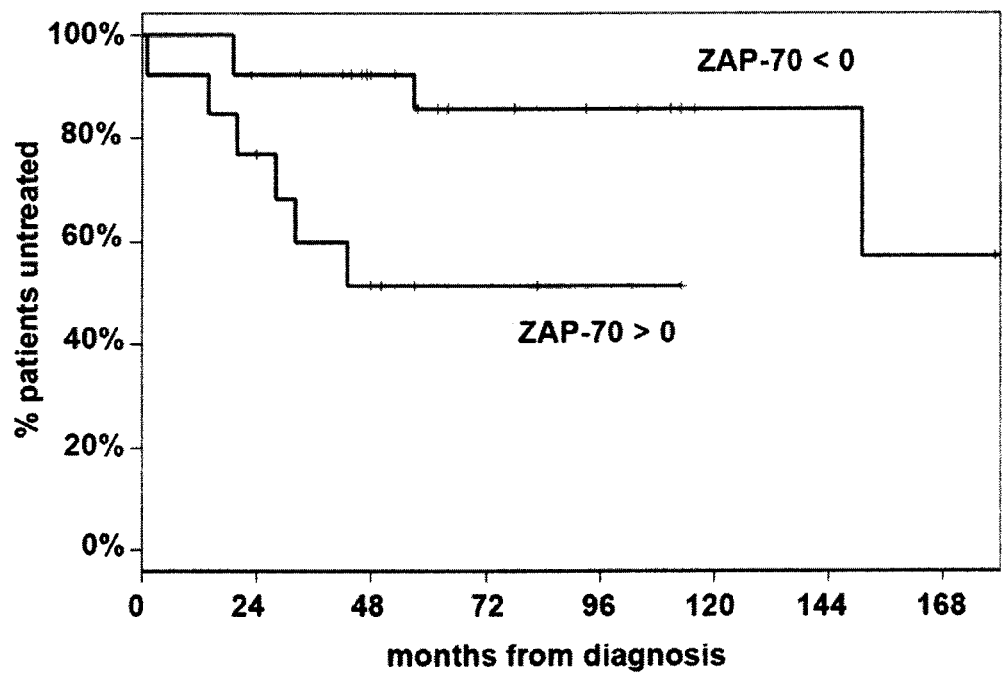

Several groups have reported the prognostic value of CD38 expression without correlating it with IgVH mutational status (Hamblin et al., *Ann. Hematol.*, 81:299, 2002; D'Arena et al., *Leuk. Lymphoma*, 42:109, 2001; Del Poeta et al., *Blood*, 98:2633, 2001' Durig et al., *Leukemia*, 16:30, 2002; Ibrahim et al., *Blood*, 98:181, 2001; Heintel et al., *Leuk. Lymphoma*, 42:1315, 2001; Morabito et al., *Leuk. Res.* 25:927, 2001). IgVH mutation status, ZAP-70 mRNA expression and CD38 surface expression were compared for their ability to predict time to disease progression, as judged by treatment requirement. At the time of last follow-up, ten patients (26%) had been treated. The CLL patients were divided into two groups based on the ZAP-70 expression cutoff described above, and these groups differed significantly in their time to treatment following diagnosis (p=0.01). ZAP-70 expression and IgVH mutation status were comparable in their ability to define CLL patients, who were different with respect to disease progression (FIGS. 3A, 3B).

Patients Discordant for IgVH Mutational Status and ZAP-70 Expression have Distinct Biological and Clinical Characteristics.

Figure 4:
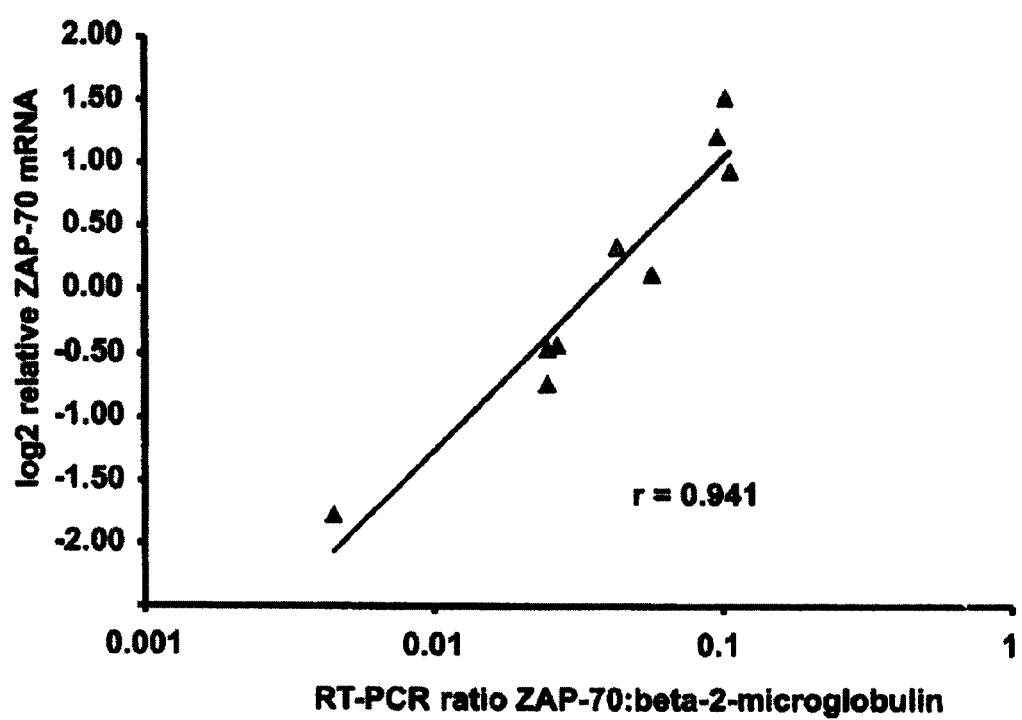
FIG. 4 is a graph showing that quantitative RT-PCR could serve as a clinical test of ZAP-70 mRNA expression. Real time quantitative RT-PCR was performed in 9 CLL samples representing the ZAP-70 mRNA expression spectrum defined by the DNA microarray analysis. ZAP-70 expression is shown relative to the expression of beta-2-microglobulin in the same sample. The Pearson coefficient for correlation between the two methods was r=0.941.

As mentioned above, 2 patients were discordant for ZAP-70 expression and IgVH mutation status, and these patients will be referred to as ZAP-70 outliers. All ZAP-70 outliers fulfilled the diagnostic criteria for CLL, and the cytogenetic abnormalities in the leukemic cells of these patients were typical of CLL (Table 2).

from the DNA microarray analysis (FIG. 4). The two assays showed an excellent correlation over a wide range of ZAP-70 mRNA levels. These results confirm the quantitative nature of the DNA microarray measurements, and suggest that a quantitative RT-PCR assay might be suitable for measuring ZAP-70 expression in a clinical setting. However, this assay requires that the leukemic cells be purified, since ZAP-70 is highly expressed in T cells.

Figure 5A:
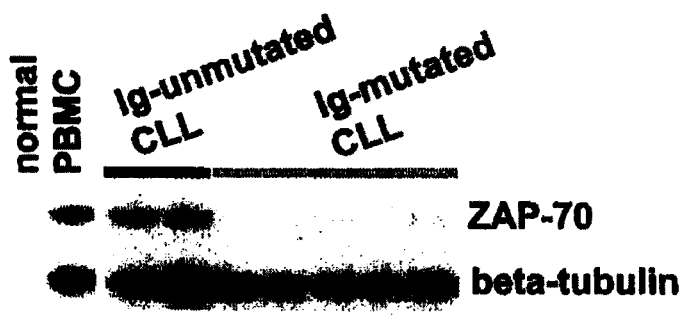
FIGS. 5A and B is a series of digital images showing that ZAP-70 protein expression can distinguish CLL subtypes and could serve as a clinical test.

The possibility that ZAP-70 protein levels could be used for a clinical diagnostic test was also demonstrated. Western blots of lysates of $CD19^+$ CLL cells revealed high levels of ZAP-70 protein expression in Ig-unmutated CLL samples compared with the relatively low levels in Ig-mutated CLL samples (FIG. 5A). Since this assay quantitates ZAP-70 protein in a population of cells, T cells were removed given their high ZAP-70 protein expression.

Figure 5B:
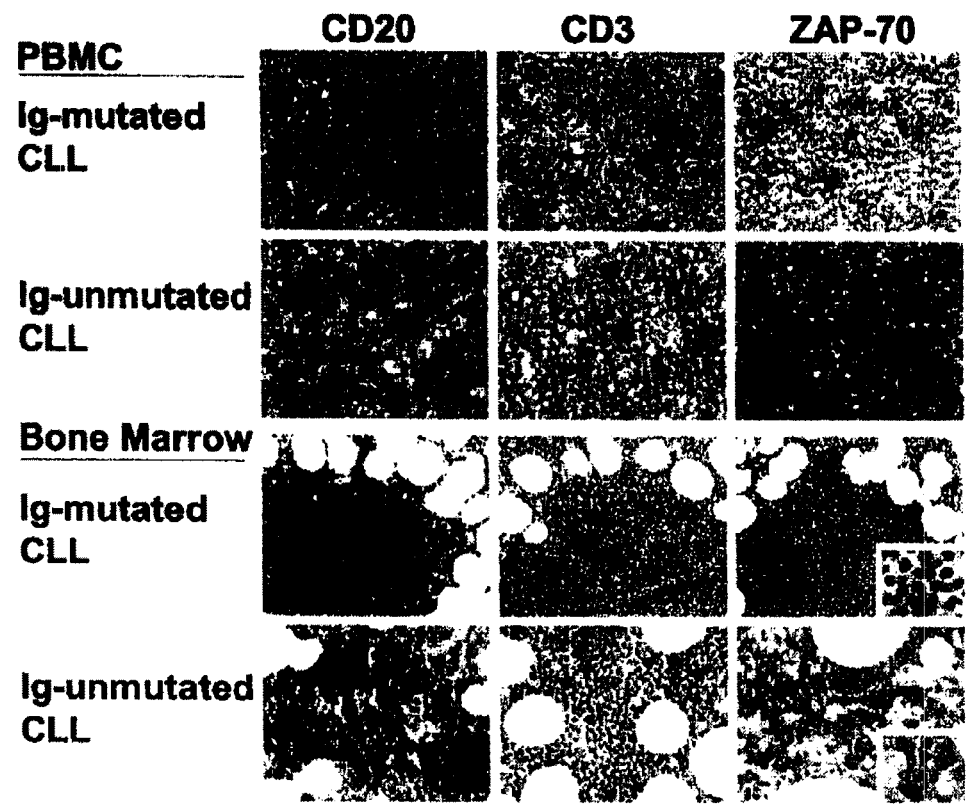
In FIG. 5B, ZAP-70 can be detected by immunohistochemistry in clinical samples. PBMC (upper half) were embedded in a fibrin clot, fixed and processed by standard techniques. PBMC and routine bone marrow trephine biopsies (lower half) were stained with CD20 demonstrating involvement by B cell CLL (B-CLL), and CD3, which stains interspersed T-cells. ZAP-70 was positive in T cells and Ig-unmutated CLL cells.

To demonstrate that ZAP-70 protein expression is detectable by immunohistochemistry, peripheral blood and routine bone marrow biopsy samples from CLL patients (FIG. 5B) were studied. In all samples, T cells stained strongly for ZAP-70, as expected. In samples from Ig-mutated CLL patients, the leukemic cells were negative or weak for ZAP-70 staining whereas the interspersed T cells were strongly positive. In samples from Ig-unmutated CLL, both the leukemic cells and the T cells had readily detectable staining.

ZAP-70 expression in 100 clinical samples from 43 patients was analyzed. In a blinded analysis, a pathologist assigned 37 of the 43 patients (86%) correctly to the IgVH mutation subtype based on ZAP-70 staining by immunohistochemistry. Two misclassified patients were ZAP-70 outliers in the DNA microarray analysis and used the mutated VH3-21 IgVH gene. Thus, in these patients the immunohistochemistry was in accord with the mRNA measurement. Interestingly, in two further misclassified cases, ZAP-70 was positive only in a subset of the leukemic cells comprising less than 25% of the sample. This finding indicates clonal heterogene-

TABLE 2

Characteristics of patients discordant for mutational status and ZAP-70 expression.

| CLL # | Sex/Age | IgVH | IgVH gene | ZAP-70 mRNA | CD 38 positive | Cyto-genetics | Clinical course | Months to therapy |
|---|---|---|---|---|---|---|---|---|
| M2 | F/54 | 96% | 3-21 | (+) | 83% | 13q- | stable | n.e. |
| M4 | M/82 | 95% | 3-21 | (+) | 18% | normal | treated | 20 |

IgVH: % homology to germline IgVH gene; ZAP-70 mRNA expression as determined by microarray analysis; % CD38 positive (i.e. staining above isotype control) by flow cytometry; +12: trisomy 12; 13q-: 13q deletion; 11q-: 11q deletion; n.e.: not evaluable.

Intriguingly, the CLL cells of the two outlier patients expressed a mutated VH3-21 gene, and these were the only cases in this series that utilized this IgVH gene. This finding is notable since expression of a mutated VH3-21 gene has been associated with progressive disease and may represent a biologically distinct subset of Ig-mutated CLL.

ZAP-70 Assays for Potential Clinical Application

The findings outlined above demonstrate that ZAP-70 mRNA expression, as measured by DNA microarrays, can be used to assign the majority of CLL patients to the correct IgVH mutational subtype and can identify patient subsets that have distinct treatment requirements. A clinical test based on ZAP-70 expression would therefore be a useful adjunct in patient management.

To this end, a quantitative RT-PCR assay for ZAP-70 expression was devised, and the quantitation of ZAP-70 mRNA levels by this method was compared with the results ity in these patients and could be of biologic significance. The two remaining misclassified cases were low for ZAP-70 mRNA expression and therefore were false positive by immunohistochemistry.

ZAP-70 Expression by Flow Cytometry.

Flow cytometry for surface markers is widely used in the diagnosis of CLL/SLL. A T cell line, which expresses ZAP-70, and a B-cell line, which is negative for ZAP-70, were used to establish flow cytometry conditions for ZAP-70, which due to its intracellular location is more difficult to detect. Using clinical samples the detection of ZAP-70 is currently less reliable. Optimization of fixation and permeabilization conditions and fluorescence coupled antibodies against ZAP-70 will increase the reliability of this assay and could be combined in a diagnostic kit. Similarly, some clinical laboratories might prefer immunocytochemistry, to which the same considerations apply.

ZAP-70 Protein Expression is a Clinically Useful Prognostic Marker and Correlates with IgVH Gene Mutation Status.

It is disclosed herein that ZAP-70 mRNA expression is an excellent surrogate marker for the distinction between the Ig-mutated and Ig-unmutated CLL subtypes and can identify patient groups with divergent clinical courses. ZAP-70 expression assigned 93% of the patients studied to the correct Ig mutation subtype. No other gene represented on the microarrays was as good as ZAP-70 in making this CLL subtype distinction, nor could any other gene improve the predictive power of ZAP-70. High ZAP-70 expression identified a clinically progressive form of CLL. By contrast, patients whose leukemic cells had low ZAP-70 expression had an indolent disease.

Hence ZAP-70 expression is believed to be a useful clinical test to guide treatment decisions. The measurement of ZAP-70 expression had a relatively low false positive rate compared to CD38. Early treatment may be beneficial for patients whose CLL cells have high ZAP-70 expression. By contrast, patients whose CLL cells have low ZAP-70 expression may be managed best by delaying treatment for as long as possible. Other prognostic markers such as chromosomal abnormalities (i.e. 11q or 17p deletion) can also be taken into consideration when designing protocols for stratifying the treatment of CLL patients.

ZAP-70 expression can be evaluated in a clinical diagnostic laboratory using a variety of approaches. A strong correlation between the ZAP-70 mRNA levels measured by DNA microarray and by quantitative RT-PCR was demonstrated (see Examples 1 and 2, above). Quantitative PCR assays have exceedingly low variation in measurement, and thus are ideal for accurately discriminating the CLL subtypes based on ZAP-70 expression. It was also demonstrated that ZAP-70 protein expression, as detected by an immunohistochemical assay, correlated well with Ig mutational status. A protein expression assay could be readily performed without purification of the CLL cells.

Thus, testing for ZAP-70 expression is an easily performed clinical assay to distinguish prognostic groups of CLL/SLL. Compared to RNA/DNA based techniques or western blots, the use of immunohistochemistry, flow cytometry, or immunofluorescence has several advantages. First, these techniques are in routine use in clinical laboratories. They do not require extensive purification of cells prior to analysis and several proteins of interest can be analyzed concomitantly. These tests lend themselves well to the development of diagnostic kits that will help to make the test widely available and will increase reliable performance of the assays. An alternative, complementary approach is quantitative ELISA to measure the total amount of ZAP-70 in a blood sample.

Example 3

Methods of Making Human ZAP-70 cDNA

The following example provides representative techniques for preparing cDNA.

Total RNA is extracted from human cells by any one of a variety of methods well known to those of ordinary skill in the art. Sambrook et al. (*In Molecular Cloning: A Laboratory Manual*, CSHL, New York, 1989) and Ausubel et al. (*In Current Protocols in Molecular Biology*, Greene Publ. Assoc. and Wiley-Intersciences, 1992) provide descriptions of methods for RNA isolation. The extracted RNA is then used as a template for performing reverse transcription-polymerase chain reaction (RT-PCR) amplification of cDNA. Methods and conditions for RT-PCR are described, for instance, in Kawasaki et al., (In *PCR Protocols, A Guide to Methods and Applications*, Innis et al. (eds.), 21-27, Academic Press, Inc., San Diego, Calif., 1990).

The selection of amplification primers is made according to the portion(s) of the cDNA that is to be amplified. Primers may be chosen to amplify a segment of a cDNA or the entire cDNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, a human ZAP-70 cDNA molecule is amplified using the primers and conditions described in Example 1.

Those primers and conditions are illustrative only; one skilled in the art will appreciate that many different primers may be derived from the provided cDNA sequence in order to amplify particular regions of ZAP-70 cDNA, as well as the complete sequence of the human ZAP-70 cDNA.

Re-sequencing of PCR products obtained by these amplification procedures is advantageous to facilitate confirmation of the amplified sequence and provide information about natural variation of this sequence in different populations or species. Oligonucleotides derived from the provided ZAP-70 sequences may be used in such sequencing methods.

Orthologs of human ZAP-70 can be cloned in a similar manner, where the starting material consists of cells taken from a non-human species. Orthologs will generally share at least 65% sequence identity with the disclosed human ZAP-70 cDNA. Where the non-human species is more closely related to humans, the sequence identity will in general be greater. Closely related orthologous ZAP-70 molecules may share at least 70%, at least 75%, at least 80% at least 85%, at least 90%, at least 91%, at least 93%, at least 95%, or at least 98% sequence identity with the disclosed human sequences.

Oligonucleotides derived from the human ZAP-70 cDNA sequence, or fragments of this cDNA, are encompassed within the scope of the present disclosure. Such oligonucleotides may comprise a sequence of at least 15 consecutive nucleotides of the ZAP-70 nucleic acid sequence. If these oligonucleotides are used with an in vitro amplification procedure (such as PCR), lengthening the oligonucleotides may enhance amplification specificity. Thus, oligonucleotide primers comprising at least 25, 30, 35, 40, 45 or 50 consecutive nucleotides of these sequences may be used. These primers for instance may be obtained from any region of the disclosed sequences. By way of example, the human ZAP-70 cDNA, ORF and gene sequences may be apportioned into about halves or quarters based on sequence length, and the isolated nucleic acid molecules (e.g., oligonucleotides) may be derived from the first or second halves of the molecules, or any of the four quarters Nucleic acid molecules may be selected that comprise at least 15, 20, 23, 25, 30, 35, 40, 50 or 100 consecutive nucleotides of any of these or other portions of the human ZAP-70 cDNA. Thus, representative nucleic acid molecules might comprise at least 15 consecutive nucleotides of the human ZAP-70 cDNA (SEQ ID NO: 1).

Example 4

Expression of ZAP-70 Protein

The expression and purification of the ZAP-70 protein, and fragments thereof, are carried out using standard laboratory techniques. Purified human ZAP-70 protein (or fragments thereof) may be used for functional analyses, drug development, testing and analysis, antibody production, diagnostics, and patient therapy. Furthermore, the DNA sequence of the ZAP-70 cDNA can be manipulated in studies to understand the expression of the gene and the function of its product. Mutant forms of the human ZAP-70 may be isolated based upon information contained herein, and may be studied in order to detect alteration in expression patterns in terms of relative quantities, cellular localization, tissue specificity and functional properties of the encoded mutant ZAP-70 protein.

Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to ZAP-70 proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence. Such antibodies may be specific for epitope tags, which can be added to the expression construct for identification an/or purification purposes.

Intact native protein may also be produced in *E. coli* in large amounts for functional studies. Methods and plasmid vectors for producing fusion proteins and intact native proteins in bacteria are described in Sambrook et al. (Sambrook et al., In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). ZAP-70 fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants, and animals (Pursel et al., *Science* 244:1281-1288, 1989), which cells or organisms are rendered transgenic by the introduction of the heterologous ZAP-70 cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with nucleic acid amplification.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses, such as papilloma (Sarver et al., *Mol. Cell. Biol.* 1:486-496, 1981) or Epstein-Barr (Sugden et al., *Mol. Cell. Biol.* 5:410-413, 1985). Alternatively, one can also produce cell lines that have integrated the vector into genomic DNA. Both of these types of cell lines produce the gene product on a continuous basis. One can also produce cell lines can also produced that have amplified the number of copies of the vector (and therefore of the cDNA as well) to create cell lines that can produce high levels of the gene product (Alt et al., *J. Biol. Chem.* 253:1357-1370, 1978).

The transfer of DNA into eukaryotic, in particular human or other mammalian cells, is now a conventional technique. Recombinant expression vectors can be introduced into the recipient cells as pure DNA (transfection) by, for example, precipitation with calcium phosphate (Graham and vander Eb, *Virology* 52:466, 1973) or strontium phosphate (Brash et al., *Mol. Cell. Biol.* 7:2013, 1987), electroporation (Neumann et al., *EMBO J.* 1:841, 1982), lipofection (Feigner et al., *Proc. Natl. Acad. Sci. USA* 84:7413, 1987), DEAE dextran (Mc-Cuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Techniques of use in packaging long transcripts can be found in Kochanek et al. (*Proc. Natl. Acad. Sci. USA* 93:5731-5739, 1996) Parks et al. (*Proc. Natl. Acad. Sci. USA* 93:13565-13570, 1996) and Parks and Graham (*J. Virol.* 71:3293-3298, 1997). ZAP-70 encoding sequences can also be delivered to target cells in vitro via non-infectious systems, for instance liposomes.

These eukaryotic expression systems can be used for studies of ZAP-70 encoding nucleic acids and mutant forms of these molecules, the ZAP-70 protein and mutant forms of this protein. Such uses include, for example, the identification of regulatory elements located in the 5' region of the ZAP-70 gene on genomic clones that can be isolated from human genomic DNA libraries using the information contained herein. The eukaryotic expression systems also may be used to study the function of the normal complete protein, specific portions of the protein, or of naturally occurring or artificially produced mutant proteins, and in order to analyze and characterize inhibitory molecules that can be used to reduce the activity of ZAP-70 in vitro of in vivo.

Using the above techniques, expression vectors containing the ZAP-70 gene sequence or cDNA, or fragments or variants or mutants thereof, can be introduced into human cells, mammalian cells from other species or non-mammalian cells, as desired. The choice of cell is determined by the purpose of the treatment. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Embodiments described herein thus encompass recombinant vectors that comprise all or part of a ZAP-70 encoding sequence, such as the ZAP-70 gene or cDNA or variants thereof, for expression in a suitable host. The ZAP-70 DNA is operatively linked in the vector to an expression control sequence in the recombinant DNA molecule so that the ZAP-70 polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with a vector, may be selected from the group consisting of *E. coli*, *Pseudomonas*, *Bacillus subtilis*, *Bacillus stearothermophilus* or other bacilli; other bacteria; yeast; fungi; insect; mouse or other animal; or plant hosts; or human tissue cells.

It is appreciated that for mutant or variant ZAP-70 DNA sequences, similar systems are employed to express and produce the mutant product.

Example 5

Production of an Antibody to ZAP-70 Protein or Protein Fragments

Monoclonal or polyclonal antibodies may be produced to either the normal ZAP-70 protein or mutant forms of this protein. Optimally, antibodies raised against the ZAP-70 protein would specifically detect the ZAP-70 protein. That is, such antibodies would recognize and bind the ZAP-70 protein and would not substantially recognize or bind to other proteins found in human cells. Antibodies the human ZAP-70 protein may recognize ZAP-70 from other species, such as murine ZAP-70, and vice versa.

The determination that an antibody specifically detects the ZAP-70 protein is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects the ZAP-70 protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the ZAP-70 protein will, by this technique, be shown to bind to the ZAP-70 protein band (which will be localized at a given position on the gel determined by its molecular weight, which is approximately 125 kDa based on gel-mobility estimation for murine ZAP-70. Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody—ZAP-70 protein binding.

Substantially pure ZAP-70 protein suitable for use as an immunogen can be isolated from the transfected or transformed cells as described above. The concentration of protein in the final preparation is adjusted, for example, by concentration on an Amicon® (Millipore, Bedford, Mass.) or similar filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the ZAP-70 protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess un-fused cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol.* 70(A):419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 4), which optionally can be modified to enhance immunogenicity. Effective polyclonal antibody production is affected by many factors related both to the antigen and the host species. For example, small molecules tend to be less immunogenic than others and may require the use of carriers and adjuvant, examples of which are known. Also, host animals vary in response to site of inoculations and dose, with either inadequate or excessive doses of antigen resulting in low titer antisera. A series of small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof begins to fall, as determined semi-quantitatively (for example, by double immunodiffusion in agar against known concentrations of the antigen). See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the ZAP-70 protein is to use synthetic peptides synthesized on a commercially available peptide synthesizer based upon the predicted amino acid sequence of the ZAP-70 protein. Polyclonal antibodies can be generated by injecting such peptides into, for instance, rabbits.

D. Antibodies Raised by Injection of ZAP-70 Encoding Sequence

Antibodies may be raised against the ZAP-70 protein by subcutaneous injection of a recombinant DNA vector that expresses the ZAP-70 protein into laboratory animals, such as mice. Delivery of the recombinant vector into the animals may be achieved using a hand-held form of the Biolistic system (Sanford et al., *Particulate Sci. Technol.* 5:27-37, 1987), as described by Tang et al. (*Nature* 356:152-154, 1992). Expression vectors suitable for this purpose may include those that express the ZAP-70 encoding sequence under the transcriptional control of either the human β-actin promoter or the cytomegalovirus (CMV) promoter.

Antibody preparations such as those prepared according to these protocols are useful in quantitative immunoassays which determine concentrations of antigen-bearing substances in biological samples; they are also used semi-quantitatively or qualitatively to identify the presence of antigen in a biological sample. Alternatively, commercially available antibodies directed against ZAP-70, such as those listed in Table 1 above, may be used in quantitative and qualitative immunoassays to identify the presence of the antigen in a biological sample.

Example 6

Nucleic Acid-Based
Diagnosis/Detection/Discrimination

The Ig-unmutated CLL-related nucleic acid molecules provided herein, and combinations of these molecules, can be used in methods of genetic testing for diagnosing, detecting, and/or discriminating between CLL/SLL clinical subgroups or prognosis owing to expression abnormalities in the nucleic acid molecule(s) (e.g., over- or under-expression in comparison to a control or baseline). For such procedures, a biological sample of the subject, which biological sample contains either DNA or RNA derived from the subject, is assayed for over- or under-expression of an Ig-unmutated CLL-related nucleic acid molecule. Regulatory regions of a gene encoding an Ig-unmutated CLL-related nucleic acid molecule, such as the enhancer or promoter regions, may also be assayed for their involvement in the over- or under-expression of an Ig-unmutated CLL-related nucleic acid molecule. Suitable biological samples include samples containing genomic DNA or RNA (including mRNA), obtained from cells of a subject, such as those present in peripheral blood, bone marrow, urine, saliva, tissue biopsy, surgical specimen, amniocentesis samples and autopsy material. Biological samples can be obtained from normal, healthy subjects or from subjects who are predisposed to or who are suffering from a leukemia such as, but not limited to, CLL.

The detection in the biological sample of over- or under-expression of one or more Ig-unmutated CLL-related nucleic acid molecule(s), may be performed by a number of methodologies, examples of which are provided.

Over- or under-expression of an Ig-unmutated CLL-related molecule can be detected by measuring the cellular level of Ig-unmutated CLL-related nucleic acid molecule-specific mRNA. mRNA can be measured using techniques well known in the art, including for instance Microarray analysis, Northern analysis, RT-PCR and mRNA in situ hybridization. Details of representative mRNA analysis procedures can be found, for instance, in Example 1 and Sambrook et al. (ed.), *Molecular Cloning: A Laboratory Manual*, 2nd ed., vol. 1-0.3, Cold Spring Harbor Laboratory Press, Cold Spring Harbor, N.Y., 1989. Details of representative microarray analysis procedures can be found in Example 1, above.

Oligonucleotides used in the above procedures can be labeled radioactively with isotopes (such as $^{32}P$) or non-radioactively, with tags such as biotin or fluorescent dyes (Ward and Langer, *Proc. Natl. Acad. Sci. USA* 78:6633-6657, 1981), and hybridized to individual DNA samples immobilized on membranes or other solid supports, for example by dot-blot or transfer from gels after electrophoresis. Quantitative or semi-quantitative PCR can also be used to measure the amount of an Ig-unmutated CLL-related molecule cDNA in a sample using Ig-unmutated CLL-related molecule oligonucleotide primers. Visualization methods such as autoradiography or fluorometric (Landegren et al., *Science* 242:229-

237, 1989) or colorimetric reactions (Gebeyehu et al., *Nucleic Acids Res.* 15:4513-4534, 1987) can be used to detect a signal and the signals quantitated using, for instance, a spectrophotometer, a scintillation counter, a densitometer or a Phosphorimager™ imaging device (Amersham Biosciences). The Phosphorimager™ is able to analyze both DNA and protein samples from blots and gels using autoradiographic, direct fluorescence or chemifluorescence detection. Since the Phosphorimager™ is more sensitive than ordinary x-ray film, exposure times can be reduced up to ten-fold and signal quantitation of both weak and strong signals on the same blot is possible. Images can be visualized and evaluated with the aid of computer programs such as ImageQuant™.

The nucleic acid-based diagnostic methods of this disclosure are predictive of CLL disease status, severity, or category. Cells of any samples that demonstrate abnormal levels (e.g., through over- or under-expression) of nucleotide sequences that share homology with the Ig-unmutated CLL-related nucleic acids disclosed herein are aggressive tumor cells, and result in decreased survival, increased metastasis, and overall worsened prognosis.

Example 7

ZAP-70 Protein

Another method of discriminating between clinical subgroups of CLL/SLL is to examine, and in some instances quantitate (either comparatively or in absolute terms), the level of ZAP-70 protein in the cells of a subject. This diagnostic tool would be useful for detecting increased levels of the ZAP-70 protein that result from, for example, mutations in the promoter regions of the ZAP-70 gene or mutations within the coding region of the gene. Alternatively, duplications of the ZAP-70 gene may be detected as an increase in the expression level of this protein. The determination of increased ZAP-70 protein levels can be used in conjunction with the determination of ZAP-70 mRNA expression levels by the methods outlined above.

The availability of antibodies specific to the ZAP-70 protein will facilitate the examination of cellular ZAP-70 protein by one of a number of immunoassay methods, which are well known in the art and are presented herein and in, for instance, Harlow and Lane (*Antibodies, A Laboratory Manual*, CSHL, New York, 1988).

For the purposes of examining the ZAP-70 protein, a biological sample of the subject is used, which sample includes cellular proteins. Such a biological sample may be obtained from body cells, such as those present in peripheral blood, urine, saliva, tissue biopsy, amniocentesis samples, surgical specimens and autopsy material. Biological samples can be obtained from normal, healthy subjects or from subjects who are predisposed to or who are suffering from a leukemia such as, but not limited to, CLL.

Antibodies can be used to assess the presence or absence of ZAP-70 in cultured cells or primary cells. The determination that an antibody specifically detects the ZAP-70 protein is made by any one of a number of standard immunoassay methods; for instance, the Western blotting technique (Sambrook et al., In *Molecular Cloning: A Laboratory Manual*, CSHL, New York, 1989). In one embodiment, it is determined whether a given antibody preparation (such as one produced in a mouse) specifically detects the ZAP-70 protein by Western blotting. In one specific, non-limiting embodiment total cellular protein is extracted from human cells (for example, lymphocytes) and electrophoresed on a sodium dodecyl sulfate-polyacrylamide gel. In another embodiment, the cellular protein is extracted from a leukemic cell. The proteins are then transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the ZAP-70 protein will, by this technique, be shown to bind to the ZAP-70 protein band (which will be localized at a given position on the gel determined by its molecular weight, which is approximately 70 kDa based on its deduced amino acid sequence). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-ZAP-70 protein binding.

An alternative method of diagnosing ZAP-70 gene deletion, amplification, or a mutation in ZAP-70 regulatory sequences, for example the ZAP-70 promoter, is to quantitate the level of ZAP-70 protein in the cells of a subject. In one embodiment, this diagnostic tool would be useful for detecting increased levels of the ZAP-70 protein that result from, for example, mutations in the promoter regions of the ZAP-70 gene. In another embodiment, duplications of the ZAP-70 gene may be detected as an increase in the expression level of this protein. The determination of increased ZAP-70 protein levels would be an alternative or supplemental approach to the direct determination of ZAP-70 gene duplication or mutation status by the methods outlined above.

The availability of antibodies specific to the ZAP-70 protein will facilitate the quantitation of cellular ZAP-70 protein by one of a number of immunoassay methods, which are well known in the art and are presented herein and in, for instance, Harlow and Lane (*Antibodies, A Laboratory Manual*, CSHL, New York, 1988). Many techniques are commonly known in the art for the detection and quantification of antigen. In one specific, non-limiting embodiment, the purified antigen will be bound to a substrate, the antibody of the sample will bind via its Fab portion to this antigen, the substrate will then be washed and a second, labeled antibody will then be added which will bind to the Fc portion of the antibody that is the subject of the assay. The second, labeled antibody will be species specific, i.e., if the serum is from a rabbit, the second, labeled antibody will be anti-rabbit-IgG antibody. The specimen will then be washed and the amount of the second, labeled antibody that has been bound will be detected and quantified by standard methods.

Examples of methods for the detection of antibodies in biological samples, including methods employing dip strips or other immobilized assay devices, are disclosed for instance in the following patents: U.S. Pat. No. 5,965,356 (Herpes simplex virus type specific seroassay); U.S. Pat. No. 6,114, 179 (Method and test kit for detection of antigens and/or antibodies); U.S. Pat. No. 6,077,681 (Diagnosis of motor neuropathy by detection of antibodies); U.S. Pat. No. 6,057, 097 (Marker for pathologies comprising an auto-immune reaction and/or for inflammatory diseases); and U.S. Pat. No. 5,552,285 (Immunoassay methods, compositions and kits for antibodies to oxidized DNA bases).

In one embodiment, for the purposes of quantitating the ZAP-70 protein, a biological sample of the subject, as described above and which includes cellular proteins, is used. Quantitation of ZAP-70 protein can be achieved by immunoassay (for example, by ELISA), immunohistochemistry, immunofluorescence, or flow cytometry and compared to levels of the protein found in healthy cells (e.g., cells from a subject known not to suffer from CLL) followed by spectrophometry or densitometry. In one embodiment, a significant (e.g., 10% or greater, for instance, 20%, 25%, 30%, 50% or more) increase in the amount of ZAP-70 protein in the cells of a subject compared to the amount of ZAP-70 protein found in normal human cells would be taken as an indication that that a duplication or enhancing mutation had occurred. In this instance, the subject may have Ig-unmutated CLL, and clinically severe or progressive CLL.

Example 8

Suppression of ZAP-70 Expression

A reduction of ZAP-70 protein expression in a target cell may be obtained by introducing into cells an antisense or other suppressive construct based on the ZAP-70 encoding sequence, including the human ZAP-70 cDNA (SEQ ID NO: 1) or gene sequence or flanking regions thereof. For antisense suppression, a nucleotide sequence from a ZAP-70 encoding sequence, e.g. all or a portion of the ZAP-70 cDNA or gene, is arranged in reverse orientation relative to the promoter sequence in the transformation vector. Other aspects of the vector may be chosen as discussed above (Example 4).

The introduced sequence need not be the full length human ZAP-70 cDNA (SEQ ID NO: 1) or gene, and need not be exactly homologous to the equivalent sequence found in the cell type to be transformed. Thus, portions or fragments of the human cDNA (SEQ ID NO: 1) could also be used to knock out or suppress expression of the human ZAP-70 gene. Generally, however, where the introduced sequence is of shorter length, a higher degree of identity to the native ZAP-70 sequence will be needed for effective antisense suppression. The introduced antisense sequence in the vector may be at least 15 nucleotides in length, and improved antisense suppression typically will be observed as the length of the antisense sequence increases. The length of the antisense sequence in the vector advantageously may be greater than 100 nucleotides, and can be up to about the full length of the human ZAP-70 cDNA or gene. For suppression of the ZAP-70 gene itself, transcription of an antisense construct results in the production of RNA molecules that are the reverse complement of mRNA molecules transcribed from the endogenous ZAP-70 gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA. Expression of ZAP-70 can also be reduced using small inhibitory RNAs, for instance using techniques similar to those described previously (see, e.g., Tuschl et al., *Genes Dev* 13, 3191-3197, 1999; Caplen et al., *Proc. Nat.l Acad. Sci. U.S.A.* 98, 9742-9747, 2001; and Elbashir et al., *Nature* 411, 494-498, 2001).

Suppression of endogenous ZAP-70 expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haseloff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Inhibition of ZAP-70 can be achieved by using agents, such as drugs, that target the protein itself. Examples of agents that could inhibit ZAP-70 function include kinase inhibitors and molecular decoys (drugs that affect protein-protein interactions). Dominant negative mutant forms of ZAP-70 may also be used to block endogenous ZAP-70 activity.

Example 9

ZAP-70 Knockout and Overexpression Transgenic Animals

Mutant organisms that under-express or over-express ZAP-70 protein are useful for research, for instance for testing and analyzing putative pharmaceutical agents useful in controlling ZAP-70 expression or activity. Such mutants allow insight into the physiological and/or pathological role of ZAP-70 in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-ZAP-70 promoter inserted upstream of a native ZAP-70 gene would be non-native. An extra copy of a ZAP-70 gene or other encoding sequence on a plasmid, transformed into a cell, would be non-native, whether that extra copy was ZAP-70 derived from the same, or a different species.

Mutants may be, for example, produced from mammals, such as mice, that either over-express or under-express ZAP-70 protein, or that do not express ZAP-70 at all. Over-expression mutants are made by increasing the number of ZAP-70-encoding sequences (such as genes) in the organism, or by introducing an ZAP-70-encoding sequence into the organism under the control of a constitutive or inducible or viral promoter such as the mouse mammary tumor virus (MMTV) promoter or the whey acidic protein (WAP) promoter or the metallothionein promoter. Mutants that under-express ZAP-70 may be made by using an inducible or repressible promoter, by deleting the ZAP-70 gene, by destroying or limiting the function of the ZAP-70 gene, for instance by disrupting the gene by transposon insertion, or by RNA interference (RNAi).

Antisense genes may be engineered into the organism, under a constitutive or inducible promoter, to decrease or prevent ZAP-70 expression, as discussed above in Example 15.

A gene is "functionally deleted" when genetic engineering has been used to negate or reduce gene expression to negligible levels. When a mutant is referred to in this application as having the ZAP-70 gene altered or functionally deleted, this refers to the ZAP-70 gene and to any ortholog of this gene. When a mutant is referred to as having "more than the normal copy number" of a gene, this means that it has more than the usual number of genes found in the wild-type organism, e.g., in the diploid mouse or human.

In *Caenorhabditis elegans*, double stranded RNA (dsRNA) mediated gene silencing, RNAi (Fire et al., *Nature* 391, 806-811, 1998) has been applied to generate "somatic knockouts" for the functional analysis of genes (Fraser et al., *Nature* 408, 325-330, 2000; Gonczy et al., *Nature* 408, 331-336, 2000). In mammalian cells, it has recently been demonstrated that synthetic 20-23 nucleotide (nt) dsRNA molecules or small interfering RNAs (siRNAs) (Tuschl et al., *Genes Dev*

13, 3191-3197, 1999) can induce RNAi gene silencing without activation of non-specific dsRNA-dependent pathways (Caplen et al., *Proc. Nat.l Acad. Sci. U.S.A.* 98, 9742-9747, 2001; Elbashir et al., *Nature* 411, 494-498, 2001).

Several models have been put forward to explain RNAi, in particular the mechanisms by which the cleavage derived small dsRNAs or siRNAs interact with the target mRNA and thus facilitate its degradation (Hamilton et al., *Science* 286, 950, 1999; Zamore et al., *Cell* 101, 25, 2000; Hammond et al., *Nature* 404, 293, 2000; Yang et al., *Curr. Biol.* 10, 1191, 2000; Elbashir et al., *Genes Dev.* 15, 188, 2001; Bass *Cell* 101, 235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of ~21-23 nts in the region corresponding to the input dsRNA (Zamore et al., *Cell* 101, 25, 2000), with the exact cleavage sites corresponding to the middle of sequences covered by individual 21- or 22 nt small dsRNAS or siRNAs (Elbashir et al., *Genes Dev.* 15, 188, 2001). Although mammals and lower organisms appear to share dsRNA-triggered responses that involve a related intermediate (small dsRNAs), it is likely that there will be differences as well as similarities in the underlying mechanism.

dsRNAs can be formed from RNA oligomers produced synthetically (for technical details see material from Xeragon and Dharmacon, both available on the internet). Small dsRNAs and siRNAs can also be manufactured using standard methods of in vitro RNA production. See, for instance, methods and characteristics described in U.S. Provisional Patent Application No. 60/308,640 (filed Jul. 30, 2001, and incorporated herein by reference). In addition, the Silencer™ siRNA Construction kit (and components thereof) available from Ambion (Catalog #1620; Austin, Tex.), which employs a T7 promoter and other well known genetic engineering techniques to produce dsRNAs. Double stranded RNA triggers could also be expressed from DNA based vector systems.

A mutant mouse over-expressing ZAP-70 may be made by constructing a plasmid having the ZAP-70 gene driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which the ZAP-70 gene is deleted or otherwise disabled can be made by removing coding regions of the ZAP-70 gene from embryonic stem cells. The methods of creating deletion mutations by using a targeting vector have been described (see, for instance, Thomas and Capecch, *Cell* 51:503-512, 1987).

Example 10

Nucleic Acid-Based ZAP-70 Therapy

Gene therapy approaches for combating ZAP-70-mediated defects in subjects, such as uncontrolled or disregulated cell growth or neoplasm, are now made possible.

Retroviruses have been considered a preferred vector for experiments in gene therapy, with a high efficiency of infection and stable integration and expression (Orkin et al., *Prog. Med. Genet.* 7:130-142, 1988). The full-length ZAP-70 gene or cDNA can be cloned into a retroviral vector and driven from either its endogenous promoter or, for instance, from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

More recent developments in gene therapy techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In addition to delivery of ZAP-70 to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

Example 11

Kits

Kits are provided which contain the necessary reagents for determining abnormal expression of ZAP-70 mRNA or ZAP-70 protein. Instructions provided in the diagnostic kits can include calibration curves, diagrams, illustrations, or charts or the like to compare with the determined (e.g., experimentally measured) values or other results.

A. Kits for Detection of ZAP-70 mRNA Expression

Kits similar to those disclosed above for the detection of ZAP-70 genomic sequences can be used to detect ZAP-70 mRNA expression levels. Such kits may include an appropriate amount of one or more of the oligonucleotide primers for use in reverse transcription amplification reactions, similarly to those provided above, with art-obvious modifications for use with RNA.

In some embodiments, kits for detection of ZAP-70 mRNA expression levels may also include the reagents necessary to carry out RT-PCR in vitro amplification reactions, including, for instance, RNA sample preparation reagents (including e.g., an RNAse inhibitor), appropriate buffers (e.g., polymerase buffer), salts (e.g., magnesium chloride), and deoxyribonucleotides (dNTPs). Written instructions may also be included.

Kits in addition may include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction.

It also may be advantageous to provided in the kit one or more control sequences for use in the RT-PCR reactions. The design of appropriate positive control sequences is well known to one of ordinary skill in the appropriate art.

The kit may also include the necessary reagents to perform the purification of the clinical sample or the normalization of the amount of cells present in the sample.

Alternatively, kits may be provided with the necessary reagents to carry out quantitative or semi-quantitative Northern analysis of ZAP-70 mRNA. Such kits include, for instance, at least one ZAP-70-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme.

B. Kits For Detection of ZAP-70 Protein or Peptide Expression

Kits for the detection of ZAP-70 protein expression, include for instance at least one target protein specific binding agent (e.g., a polyclonal or monoclonal antibody or antibody fragment) and may include at least one control. The ZAP-70 protein specific binding agent and control may be contained in separate containers. The kits may also include means for detecting ZAP-70:agent complexes, for instance the agent may be detectably labeled. If the detectable agent is not labeled, it may be detected by second antibodies or protein A for example which may also be provided in some kits in one or more separate containers. Such techniques are well known.

The kit may also include the necessary reagents to perform the purification of the clinical sample or the normalization of the amount of cells present in the sample.

Additional components in some kits include instructions for carrying out the assay. Instructions will allow the tester to determine whether ZAP-70 expression levels are altered, for instance in comparison to a control sample. Reaction vessels and auxiliary reagents such as chromogens, buffers, enzymes, etc. may also be included in the kits.

By way of example only, an effective and convenient immunoassay kit such as an enzyme-linked immunosorbent assay can be constructed to test anti-ZAP-70 antibody in human serum. Expression vectors can be constructed using the human ZAP-70 cDNA to produce the recombinant human ZAP-70 protein in either bacteria or baculovirus (as described in Example 10). By affinity purification, unlimited amounts of pure recombinant ZAP-70 protein can be produced.

An assay kit could provide the recombinant protein as an antigen and enzyme-conjugated goat anti-human IgG as a second antibody as well as the enzymatic substrates. Such kits can be used to test if the patient sera contain antibodies against human ZAP-70.

This disclosure provides methods of determining or detecting disease status in a subject, particularly detecting, determining, or discriminating between clinical subgroups of CLL/SLL based on the levels of mRNA or protein levels in a biological sample from a subject. The disclosure further provides compositions for use in such methods, pharmaceutical preparations, and kits and assays. It will be apparent that the precise details of the methods and compositions described may be varied or modified without departing from the spirit of the described invention. We claim all such modifications and variations that fall within the scope and spirit of the claims below.

The invention claimed is:

1. A method of determining a predisposition to poor clinical outcome in a subject having chronic lymphocytic leukemia (CLL), comprising:
 determining in a sample comprising B-CLL cells from the subject whether the B-CLL cells are ZAP-70 positive; and
 determining that the subject has a predisposition to poor clinical outcome when the B-CLL cells are ZAP-70 positive.

2. The method of claim 1, wherein the predisposition to poor clinical outcome is correlated with the presence of Ig-unmutated CLL in the subject with CLL.

3. The method of claim 1, wherein determining whether the B-CLL cells are ZAP-70 positive comprises:
 contacting the sample from the subject with a reagent comprising a ZAP-70-specific antibody or binding fragment thereof, to form a ZAP-70:antibody complex or a ZAP-70:antibody binding fragment complex; and
 detecting the complex.

4. The method of claim 3, wherein detecting the complex comprises flow cytometry, immunocytochemistry, Western blot, or ELISA.

5. The method of claim 1, wherein the ZAP-70 comprises a polypeptide comprising the amino acid sequence of SEQ ID NO: 2.

6. The method of claim 1, further comprising determining whether the B-CLL cells overexpress a second polypeptide.

7. The method of claim 6, wherein the second polypeptide is an activation-induced C-type lectin polypeptide.

8. The method of claim 6, further comprising determining whether the B-CLL cells overexpress a third polypeptide.

9. A method of determining a predisposition to poor clinical outcome in a subject having chronic lymphocytic leukemia (CLL), comprising:
 determining in a sample comprising B-CLL cells from the subject whether the B-CLL cells express a ZAP-70 polypeptide; and
 determining that the subject has a predisposition to poor clinical outcome when the B-CLL cells express a ZAP-70 polypeptide.

10. The method of claim 9, wherein the predisposition to poor clinical outcome is correlated with the presence of Ig-unmutated CLL in the subject with CLL.

11. The method of claim 9, wherein determining whether the B-CLL cells express the ZAP-70 polypeptide comprises:
 contacting the sample from the subject with a reagent comprising a ZAP-70-specific antibody or binding fragment thereof, to form a ZAP-70:antibody complex or a ZAP-70:antibody binding fragment complex; and
 detecting the complex.

12. The method of claim 11, wherein detecting the complex comprises flow cytometry, immunocytochemistry, Western blot, or ELISA.

13. The method of claim 9, wherein the ZAP-70 polypeptide comprises a polypeptide comprising the amino acid sequence of SEQ ID NO: 2.

14. The method of claim 9, further comprising determining whether the B-CLL cells overexpress a second polypeptide.

15. The method of claim 14, wherein the second polypeptide is an activation-induced C-type lectin polypeptide.

16. The method of claim 14, further comprising determining whether the B-CLL cells overexpress a third polypeptide.

17. A method of determining a predisposition to poor clinical outcome in a subject having chronic lymphocytic leukemia (CLL), comprising:
 determining in a sample comprising B-CLL cells from the subject whether the B-CLL cells are ZAP-70 positive, wherein the ZAP-70 comprises a ZAP-70 polypeptide of SEQ ID NO: 2, and
 determining that the subject has a predisposition to poor clinical outcome when the B-CLL cells are ZAP-70 positive.

18. The method of claim 17, wherein determining whether the B-CLL cells are ZAP-70 positive comprises:
 reacting at least one ZAP-70 polypeptide of SEQ ID NO: 2 contained in the sample with a reagent comprising a ZAP-70-specific antibody to form a ZAP-70:antibody complex; and
 detecting the complex using flow cytometry, wherein presence of the complex indicates the B CLL cells are ZAP-70 positive.

19. A method of determining a predisposition to poor clinical outcome in a subject having chronic lymphocytic leukemia (CLL), comprising:
 determining in a sample comprising B-CLL cells from the subject whether the B-CLL cells express a ZAP-70 polypeptide of SEQ ID NO: 2; and
 determining that the subject has a predisposition to poor clinical outcome when the B-CLL cells express the ZAP-70 polypeptide of SEQ ID NO: 2.

20. The method of claim 19, wherein determining whether the B-CLL cells express the ZAP-70 polypeptide comprises:
 reacting at least one ZAP-70 polypeptide of SEQ ID NO: 2 contained in the sample with a reagent comprising a ZAP-70-specific antibody to form a ZAP-70:antibody complex; and
 detecting the complex using flow cytometry.

* * * * *

SEQUENCE LISTING

```
<160> NUMBER OF SEQ ID NOS: 21

<210> SEQ ID NO 1
<211> LENGTH: 2429
<212> TYPE: DNA
<213> ORGANISM: Homo sapiens

<400> SEQUENCE: 1
aataggttag tttcagacaa gcctgcttgc cggagctcag cagacaccag gccttccggg      60
caggcctggc ccaccgtggg cctcagagct gctgctgggg cattcagaac cggctctcca     120
ttggcattgg gaccagagac cccgcaagtg gcctgtttgc ctggacatcc acctgtacgt     180
ccccaggttt cgggaggccc aggggcgatg ccagaccccg cggcgcacct gcccttcttc     240
tacggcagca tctcgcgtgc cgaggccgag gagcacctga agctggcggg catggcggac     300
gggctcttcc tgctgcgcca gtgcctgcgc tcgctgggcg gctatgtgct gtcgctcgtg     360
cacgatgtgc gcttccacca cttttcccatc gagcgccagc tcaacggcac ctacgccatt     420
gccggcggca aagcgcactg tggaccggca gagctctgcg agttctactc gcgcgacccc     480
gacgggctgc cctgcaacct gcgcaagccg tgcaaccggc cgtcgggcct cgagccgcag     540
ccgggggtct tcgactgcct gcgagacgcc atggtgcgtg actacgtgcg ccagacgtgg     600
aagctggagg gcgaggccct ggagcaggcc atcatcagcc aggccccgca ggtggagaag     660
ctcattgcta cgacggccca cgagcggatg ccctggtacc acagcagcct gacgcgtgag     720
gaggccgagc gcaaactttta ctctggggcg cagaccgacg gcaagttcct gctgaggccg     780
```

```
cggaaggagc agggcacata cgccctgtcc ctcatctatg ggaagacggt gtaccactac    840
ctcatcagcc aagacaaggc gggcaagtac tgcattcccg agggcaccaa gtttgacacg    900
ctctggcagc tggtggagta tctgaagctg aaggcggacg ggctcatcta ctgcctgaag    960
gaggcctgcc ccaacagcag tgccagcaac gcctcagggg ctgctgctcc cacactccca   1020
gcccacccat ccacgttgac tcatcctcag agacgaatcg acaccctcaa ctcagatgga   1080
tacacccctg agccagcacg cataacgtcc ccagacaaac cgcggccgat gcccatggac   1140
acgagcgtgt atgagagccc ctacagcgac ccagaggagc tcaaggacaa gaagctcttc   1200
ctgaagcgcg ataacctcct catagctgac attgaacttg gctgcggcaa ctttggctca   1260
gtgcgccagg gcgtgtaccg catgcgcaag aagcagatcg acgtggccat caaggtgctg   1320
aagcagggca cggagaaggc agacacggaa gagatgatgc gcgaggcgca gatcatgcac   1380
cagctggaca ccctacat cgtgcggctc attggcgtct gccaggccga ggccctcatg   1440
ctggtcatgg agatggctgg gggcgggccg ctgcacaagt tcctggtcgg caagagggag   1500
gagatccctg tgagcaatgt ggccgagctg ctgcaccagg tgtccatggg gatgaagtac   1560
ctggaggaga gaactttgt gcaccgtgac ctggcggccc gcaacgtcct gctggttaac   1620
cggcactacg ccaagatcag cgactttggc ctctccaaag cactgggtgc cgacgacagc   1680
tactacactg cccgctcagc agggaagtgg ccgctcaagt ggtacgcacc cgaatgcatc   1740
aacttccgca agttctccag ccgcagcgat gtctggagct atggggtcac catgtgggag   1800
gccttgtcct acggccagaa gccctacaag aagatgaaag gccggaggt catggccttc   1860 atcgagcagg gcaagcggat ggagtgccca ccagagtgtc cacccgaact gtacgcactc   1920
atgagtgact gctggatcta caagtgggag gatcgccccg acttcctgac cgtggagcag   1980
cgcatgcgag cctgttacta cagcctggcc agcaaggtgg aagggccccc aggcagcaca   2040
cagaaggctg aggctgcctg tgcctgagct cccgctgccc aggggagccc tccacgccgg   2100
ctcttcccca ccctcagccc caccccaggt cctgcagtct ggctgagccc tgcttggttg   2160
tctccacaca cagctgggct gtggtagggg gtgtctcagg ccacaccggc cttgcattgc   2220
ctgcctggcc ccctgtcctc tctggctggg agcaggag tccgggagg gtgcggctgt   2280 gcagcctgtc ctgggctggt ggctcccgga gggccctgag ctgagggcat gcttacacg    2340 gatgccttcc cctgggccct gacattggag cctgggcatc ctcaggtggt caggcgtaga   2400
tcaccagaat aaacccagct tccctcttg                                      2429
```

<210> SEQ ID NO 2
<211> LENGTH: 619
<212> TYPE: PRT
<213> ORGANISM: Homo sapiens

<400> SEQUENCE: 2

```
Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
```

```
                85                  90                  95
Asn Leu Arg Lys Pro Cys Asn Arg Pro Ser Gly Leu Glu Pro Gln Pro
            100                 105                 110
Gly Val Phe Asp Cys Leu Arg Asp Ala Met Val Arg Asp Tyr Val Arg
            115                 120                 125
Gln Thr Trp Lys Leu Glu Gly Glu Ala Leu Glu Gln Ala Ile Ile Ser
            130                 135                 140
Gln Ala Pro Gln Val Glu Lys Leu Ile Ala Thr Ala His Glu Arg
145                 150                 155                 160
Met Pro Trp Tyr His Ser Ser Leu Thr Arg Glu Glu Ala Glu Arg Lys
                165                 170                 175
Leu Tyr Ser Gly Ala Gln Thr Asp Gly Lys Phe Leu Leu Arg Pro Arg
                180                 185                 190
Lys Glu Gln Gly Thr Tyr Ala Leu Ser Leu Ile Tyr Gly Lys Thr Val
                195                 200                 205
Tyr His Tyr Leu Ile Ser Gln Asp Lys Ala Gly Lys Tyr Cys Ile Pro
            210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Ala Pro Thr Leu Pro Ala
                260                 265                 270
His Pro Ser Thr Leu Thr His Pro Gln Arg Arg Ile Asp Thr Leu Asn
            275                 280                 285
Ser Asp Gly Tyr Thr Pro Glu Pro Ala Arg Ile Thr Ser Pro Asp Lys
            290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                325                 330                 335
Leu Leu Ile Ala Asp Ile Glu Leu Gly Cys Gly Asn Phe Gly Ser Val
                340                 345                 350
Arg Gln Gly Val Tyr Arg Met Arg Lys Lys Gln Ile Asp Val Ala Ile
            355                 360                 365
Lys Val Leu Lys Gln Gly Thr Glu Lys Ala Asp Thr Glu Glu Met Met
            370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Met Glu Met
                405                 410                 415
Ala Gly Gly Gly Pro Leu His Lys Phe Leu Val Gly Lys Arg Glu Glu
                420                 425                 430
Ile Pro Val Ser Asn Val Ala Glu Leu Leu His Gln Val Ser Met Gly
            435                 440                 445
Met Lys Tyr Leu Glu Glu Lys Asn Phe Val His Arg Asp Leu Ala Ala
450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
            500                 505                 510
```

```
Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
            565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
            595                 600                 605

Gly Ser Thr Gln Lys Ala Glu Ala Ala Cys Ala
            610                 615

<210> SEQ ID NO 3
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 3
tctccaaagc actgggtg                                                   18

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 4
agctgtgtgt ggagacaacc aag                                             23

<210> SEQ ID NO 5
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 5
ccatggactg gacctgga                                                   18

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 6
atggacatac tttgttccac                                                 20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
ccatggagtt tgggctgagc                                                 20
```

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
atgaaacacc tgtggttctt                                          20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
atggggtcaa ccgccatcct                                          20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
atgtctgtct ccttcctcat                                          20

<210> SEQ ID NO 11
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 11
acctgaggag acggtgacc                                           19

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
aggagaaagt gatggagtcg                                          20

<210> SEQ ID NO 13
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 13
cgctgcacaa gttcctggt                                           19

<210> SEQ ID NO 14
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 14
gacacctggt gcagcagct                                              19

<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
cattgctcac agggatctcc tccctct                                     27

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 16
aggtgcagct ggtgcagtct g                                           21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
aggtcaactt aagggagtct g                                           21

<210> SEQ ID NO 18
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 18
aggtgcagct ggtggagtct g                                           21

<210> SEQ ID NO 19
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 19
aggtgcagct gcaggagtcg g                                           21

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 20
aggtgcagct gctgcagtct g                                           21

<210> SEQ ID NO 21
<211> LENGTH: 21

-continued

```
<212> TYPE: DNA
<213> ORGANISM: Artificial Sequence
<220> FEATURE:
<223> OTHER INFORMATION: oligonucleotide primer

<400> SEQUENCE: 21
aggtacagct gcagcagtca g                                             21
```